(12) United States Patent
Iwahashi et al.

(10) Patent No.: US 6,599,287 B2
(45) Date of Patent: Jul. 29, 2003

(54) MEDICAL ENERGY IRRADIATION APPARATUS

(75) Inventors: Shigenobu Iwahashi, Kanagawa (JP); Shin Maki, Kanagawa (JP); Akira Sakaguchi, Kanagawa (JP)

(73) Assignee: Terumo Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/895,260

(22) Filed: Jul. 2, 2001

(65) Prior Publication Data

US 2002/0016619 A1 Feb. 7, 2002

(30) Foreign Application Priority Data

Jul. 3, 2000 (JP) ........................................ 2000-201638

(51) Int. Cl.⁷ .............................................. A61B 18/18
(52) U.S. Cl. ............................ 606/14; 606/16; 606/17; 606/13; 607/88; 607/92; 607/93; 600/101; 600/104; 600/106
(58) Field of Search ................................. 606/7, 10–19, 606/22, 23, 41, 46; 607/88, 89, 92, 93; 604/20, 21; 378/65; 600/101, 103, 104, 106–108, 114, 117, 118, 129, 142

(56) References Cited

U.S. PATENT DOCUMENTS

| | | | |
|---|---|---|---|
| 4,932,956 A | 6/1990 | Reddy et al. | |
| 5,207,672 A | 5/1993 | Roth et al. | |
| 5,292,320 A | 3/1994 | Brown et al. | |
| 5,454,807 A | * 10/1995 | Lennox et al. ................ | 606/15 |
| 5,496,308 A | 3/1996 | Brown et al. | |
| 5,800,378 A | * 9/1998 | Edwards et al. ............... | 604/22 |
| 6,007,571 A | * 12/1999 | Neilson et al. ............. | 607/105 |
| 6,379,347 B1 | * 4/2002 | Maki et al. .................... | 606/17 |

FOREIGN PATENT DOCUMENTS

| | | | | |
|---|---|---|---|---|
| EP | 0 673 627 A1 | 3/1995 | | |
| EP | 0 947 221 A2 | 10/1999 | | |
| EP | 0 960 601 A2 | 12/1999 | | |
| EP | 0 960 601 A2 | * 12/1999 | ........... | A61B/17/36 |
| EP | 1 095 671 A2 | * 5/2001 | ........... | A61N/5/06 |
| JP | 17772 A | * 1/2002 | ........... | A61F/7/12 |
| WO | WO 92/04934 A1 | 4/1992 | | |
| WO | WO 93/04727 A1 | 3/1993 | | |

* cited by examiner

Primary Examiner—Linda C. M. Dvorak
Assistant Examiner—A. Farah
(74) Attorney, Agent, or Firm—Burns, Doane, Swecker & Mathis, LLP

(57) ABSTRACT

An energy irradiation apparatus for medical treatment of tissues through irradiation of energy including a long main unit, an emitting part, a power transmission member, a drive mechanism, a first engaging member, and a second engaging is disclosed. The emitting part is disposed moveably inside a distal end of the main unit for emitting energy transmitted to a distal side from a proximal side. The power transmission member is disposed moveable inside the main unit. The emitting part is mounted to a distal end of the power transmission member. The drive mechanism reciprocates the power transmission member in a longitudinal direction of the main unit. The first engaging member is provided inside the power transmission member for receiving a drive force from the drive mechanism. The second engaging member is provided in the drive mechanism for engaging removably with the first engaging member.

22 Claims, 21 Drawing Sheets

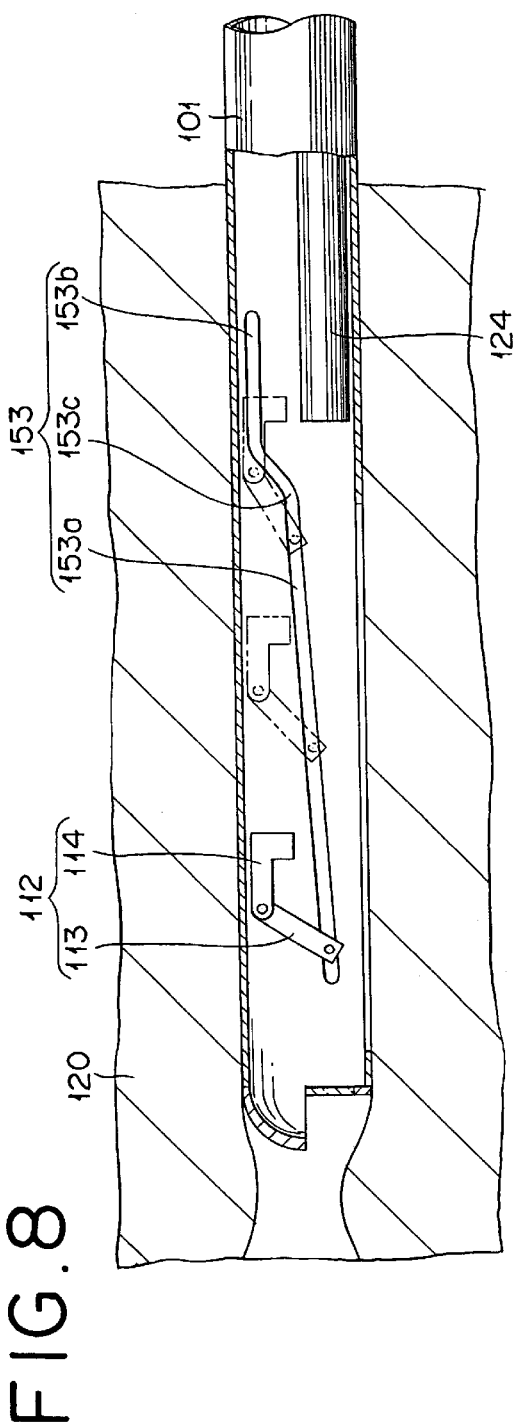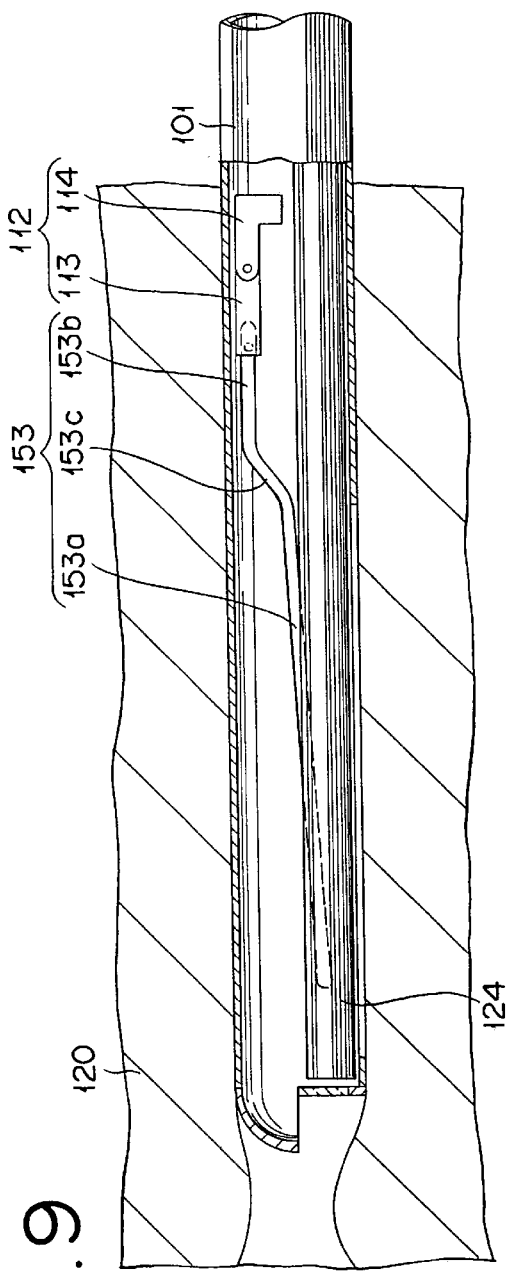
FIG. 8
FIG. 9

MEDICAL ENERGY IRRADIATION APPARATUS

BACKGROUND OF THE INVENTION

1. Field of the Invention

The invention relates to an apparatus for treating tumors such as cancer, benign prostatic hyperplasia, etc., by irradiating vital tissues with various forms of energies such as laser beams, microwaves, radio frequency, and ultrasonic waves.

2. Description of the Related Art

Various apparatuses have been known for treating lesions to reduce or eliminate them by means of heating, alteration, sphacelation, coagulation, cauterization or evaporation of the tissues of the lesions by irradiating them with energies from the emitting part encased in the distal end of a long shaft-like main unit inserted into a human body either via a body cavity or an opening produced by a small incision.

For example, in case of the treatment of benign prostatic hyperplasia, it is customary to apply a transurethral treatment since the prostate is located in the bottom of the bladder and at a position to surround the bottom of the proximal part of the urethra.

An apparatus suitable for transurethral treatments has been proposed, in which a long main unit inserted into the urethra and the emitting part is reciprocated longitudinally while changing the emitting angle of laser beams so that the laser beams can be converged on the target region, which is located deep inside the tissue. Using the particular apparatus, only the target region can be heated to a desired temperature for treatment while other regions are maintained at low temperatures However, since said apparatus requires a complicated and sizeable constitution, as it has to have a combination of a long main unit and a drive mechanism for reciprocating the emitting part inside the main unit, the long main unit is reused after cleaning and disinfection after a use. In other words, the long main unit ends up being used against multiple patients repeating cleaning and disinfection.

Consequently, the functions and performances of the apparatus degrade as the time goes on resulting from its repetitive uses, and it may gradually become incapable of providing sufficient curative effects, and increase the burden on the patient. It is also a severe burden on the clinical staff to have to clean and disinfect the apparatus completely to eliminate the concern for contamination.

Moreover, if the positioning of the distal end of the main unit is inaccurate in laser beam irradiation, it can cause either excessively overlapping irradiation on the same region or irradiation on off-target regions, in either of which a sufficient curative effect cannot be achieved, and cause additional burdens on the patient due to a prolonged treatment period. Therefore, it is desirable to locate the distal end of the main unit precisely within the urethra based on a sufficient observation in the forward direction, which is the inserting direction of the main unit, as the long main unit is being inserted into the urethra.

However, the apparatus of the prior art is built in such a way that the reflecting part of the laser beam located in the emitting part interferes with the forward viewing field. On the other hand, if the endoscope is placed in the main unit in such a way as not to interfere with the forward viewing field, the diameter of the endoscope will become limited as there is a limit to the size of the main unit. Thus, it is difficult to install an endoscope with a sufficiently clear and wide field of view.

Moreover, since the distance between the distal end of the optical fiber from which the laser beam is emitted and the reflecting part varies with the movement of the reflecting part, it is necessary to stabilize the spot diameter of the laser beam by providing a special optical system at the distal end of the optical fiber. Moreover, in order to have a variable reflection angle, it requires a complex hinge mechanism consisting of many components.

Because of such a complex constitution, it inevitably leads to degradation of functions and performances as the time goes on resulting from repeated uses, and becomes difficult to obtain desirable and sufficient curative effects, and results in an increased burden on the patient's part.

SUMMARY OF THE INVENTION

It is therefore a general object of the present invention to provide a medical energy irradiation apparatus that reduces the patient's burden.

More specifically, it is an object of the invention to provide an energy irradiation apparatus for medical treatment of tissues through irradiation of energy including a long main unit, an emitting part, a power transmission member, a drive mechanism, a first engaging member, and a second engaging. The emitting part is disposed moveably inside a distal end of the main unit for emitting energy transmitted to a distal side from a proximal side. The power transmission member is disposed moveable inside the main unit. The emitting part is mounted to a distal end of the power transmission member. The drive mechanism reciprocates the power transmission member in a longitudinal direction of the main unit. The first engaging member is provided inside the power transmission member for receiving a drive force from the drive mechanism. The second engaging member is provided in the drive mechanism for engaging removably with the first engaging member.

The objects, features, and characteristics of this invention other than those set forth above will become apparent from the description given herein below with reference to preferred embodiments illustrated in the accompanying drawings.

BRIEF DESCRIPTION OF THE DRAWINGS

FIG. 8 is a schematic illustration of assistance in explaining a position of the reflecting part when the laser beam is being radiated;

FIG. 9 is a schematic illustration of assistance in explaining a position of the reflecting part when forward view is being observed;

DETAILED DESCRIPTION OF THE PREFERRED EMBODIMENTS

The embodiments of this invention will be described below with reference to the accompanying drawings.

Figure 1:
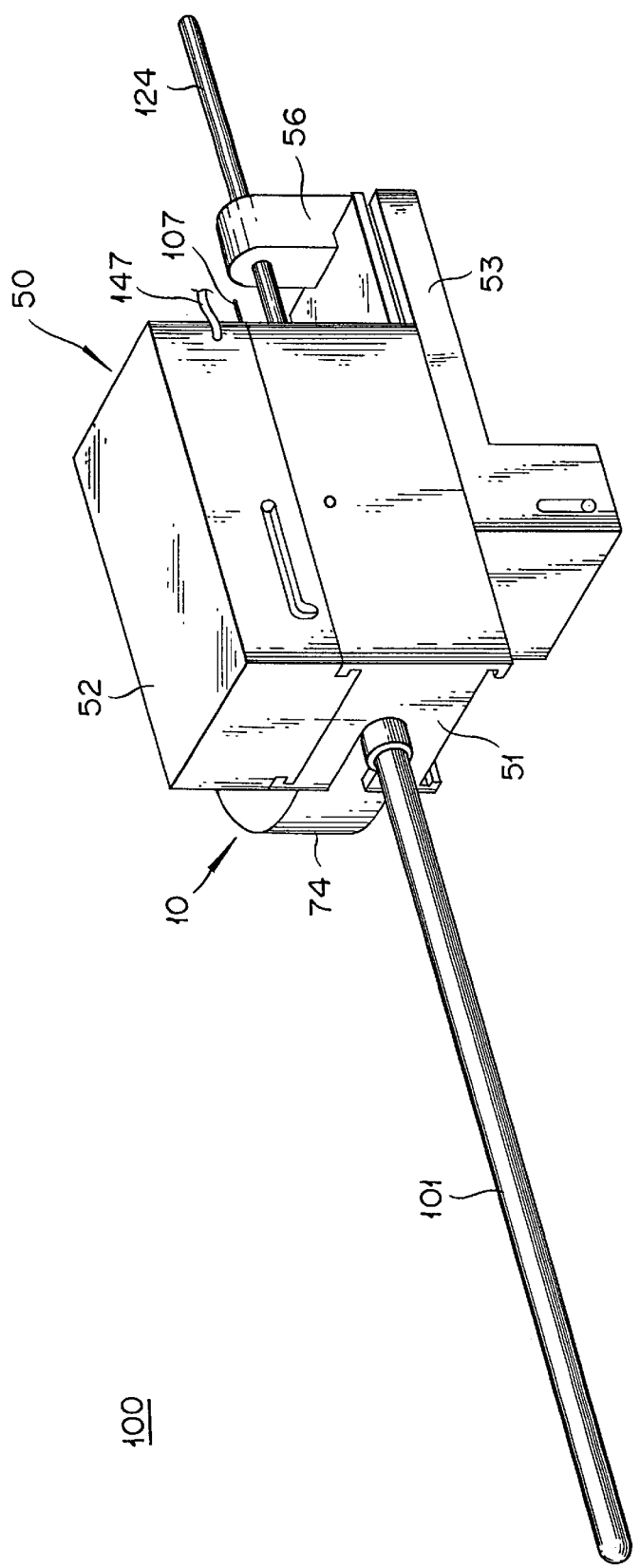
FIG. 1 is a perspective view of a laser beam irradiation apparatus according to the first embodiment of the invention.
Figure 2:
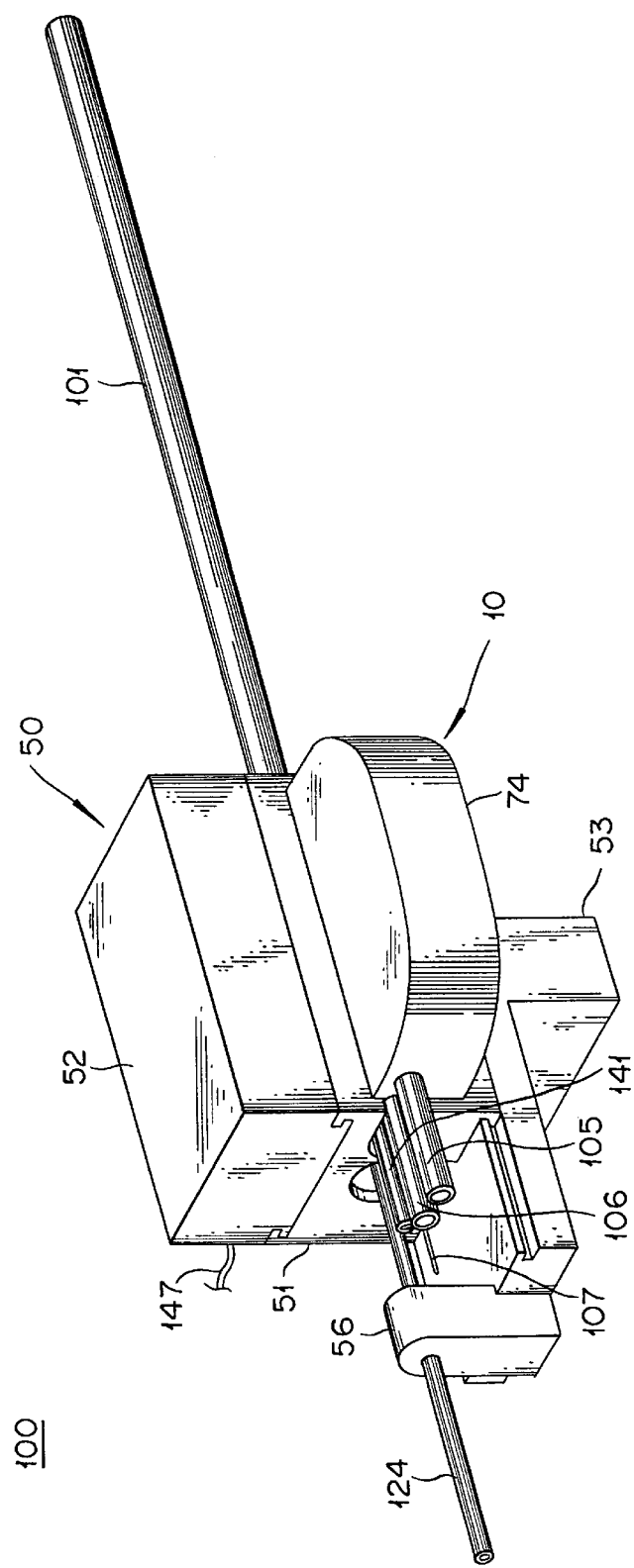
FIG. 2 is a perspective view of the apparatus viewed from the left rear side of FIG. 1.
Figure 3:
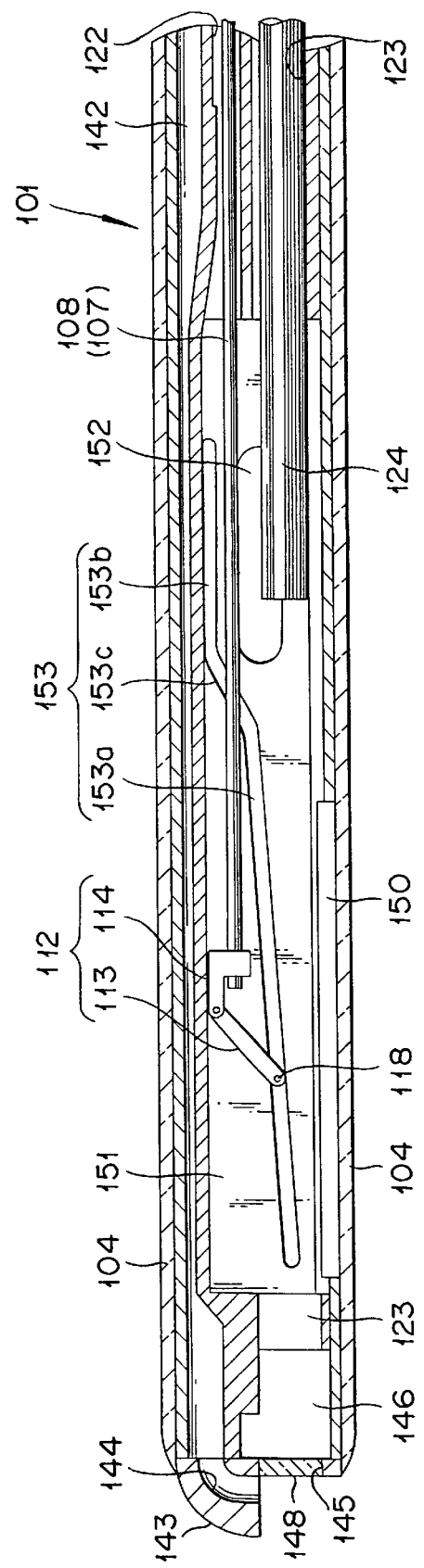
FIG. 3 is a cross section of assistance in explaining the internal constitution of the distal end of the laser beam irradiation apparatus.

A side emitting type laser beam irradiation apparatus 100 shown in FIG. 1 through FIG. 3 is used, for example, for the treatment of benign prostatic hyperplasia by irradiating tissues with laser beams. The apparatus 100 has an insertion part 10 provided with a long shaft-like main unit 101, which is to be inserted into a human body, and a proximal unit 50 provided with a drive mechanism for causing a laser emitting part 112 built into the main unit 101 to reciprocate in the longitudinal direction of the main unit 101, both of which are built to be removable. The apparatus 100 is connected to a power source (not shown) via a cord 147.

The main unit 101 has on its distal end a side window 150, which is an opening for the laser beam to pass through. The entire main unit 101 including the side window 150 is covered by a cover 104 of an excellent laser beam transparency. The distal end of the main unit 101 is sealed by a cap 143. The cap 143 is provided with a front window 145 for observing the front when the main unit 101 is inserted into the human body. A light transmitting plate 148 with a good light transmission capability in mounted on and fixed to the front window 145. Wall members 151 are fixed to inner sides of the distal end of the main unit 101 defining its inside space. The wall members 151 consist of left and right components in pairs.

An optical fiber 107 for transmitting the laser beam is placed inside the main unit 101. The optical fiber 107 inside the main unit 101, except its distal end, is entirely covered by a protective pipe 108 made of stainless steel to protect it from damage or bending. The proximal end of the optical fiber 107 is connected to a laser beam generator (not shown) via an optical connector.

The distal end of the optical fiber 107 is connected to an emitting part 112, which emits the laser beam sideways.

Figure 4:
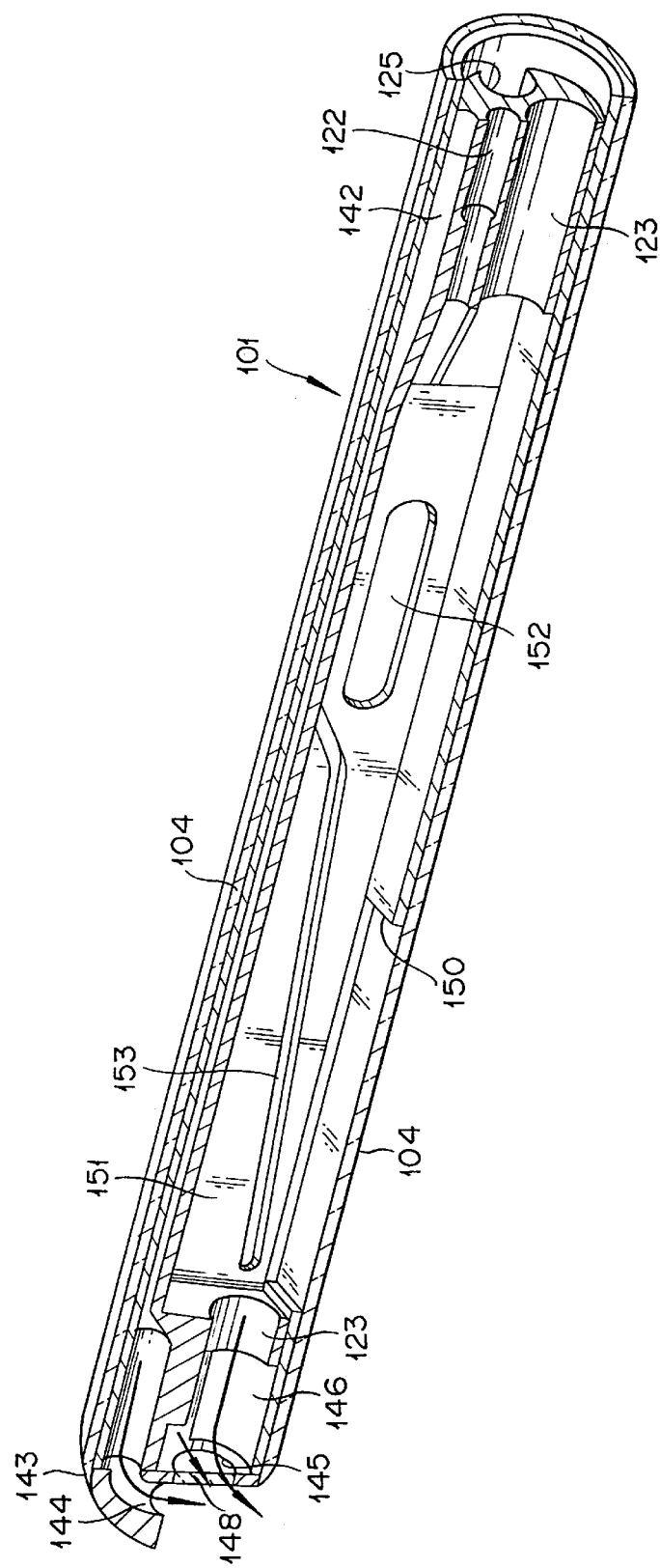
FIG. 4 is a perspective view of the distal end of the laser beam irradiation apparatus taken along the vertical plane.

As shown in FIG. 3 and FIG. 4, a lumen 122 is formed in parallel to the axis of the main unit 101. The optical fiber 107 protected by the protective pipe 108 is inserted into the lumen 122 in such a way as to be able to make a reciprocating motion. At the proximal end of the lumen 122, an O-ring (not shown) is provided to seal between the protective pipe 108 and the lumen 122 in order to prevent the leakage of the cooling water. Further, another lumen 123 is provided for an endoscope 124 to be installed and move inside it. For the sake of the simplicity of description, moving parts are not shown in FIG. 4.

The endoscope 124 is inserted from the proximal side of the apparatus 100 shown in FIG. 1, and is capable of moving inside the main unit 101 in the longitudinal direction. For example, the endoscope 124 includes a bundle of optical fibers and a protective tube and is provided with an imaging lens (not shown) provided at the distal end, or a relay lens installed inside the metal pipe. In both cases, it is desirable to have a light guide for the illumination.

The endoscope 124 has a field of view preferable for acquiring observation fields from both the side window 150 and the front window 145. Therefore, it is possible for the operator to observe the surface layer of the tissue to be irradiated with the laser beam, perform a proper positioning of the distal end of the main unit 101, and perform a visual confirmation of the laser beam irradiation position using the endoscope 124 through the side window 150 or the front window 145. Moreover, since it is possible to observe the irradiated surface continuously during the laser beam irradiation, it is possible to optimize the irradiation condition based on the actual condition.

The cooling water flows into the main unit 101 through a tube 105 by means of a cooling water circulating apparatus (not shown) and flows out from the main unit 101 via a tube 106. In other words, the cooling water circulates through the main unit 101 and cools the surface of the tissue that receive the laser beam, the laser emission end in the distal end of the main unit 101, the reflecting part, etc.

Figure 5:
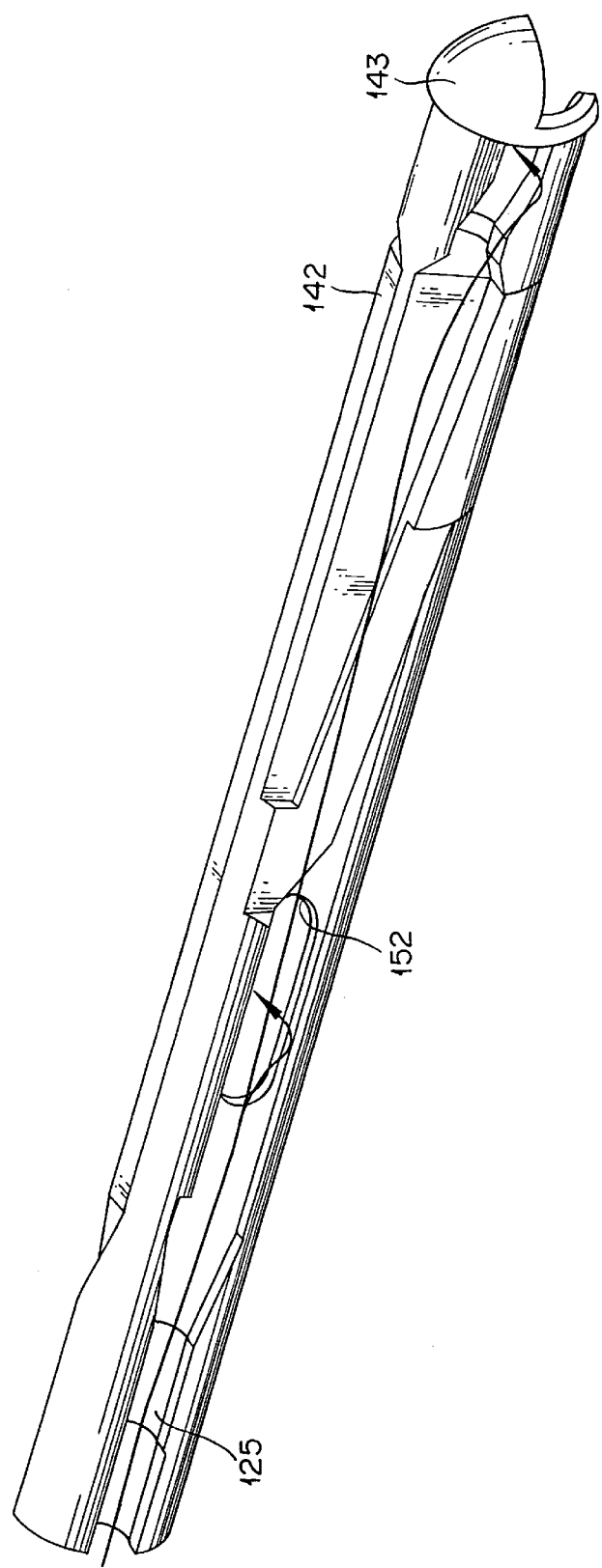
FIG. 5 is a perspective view of the apparatus viewed from the right front side of FIG. 4.

As indicated by the arrows shown in FIG. 4 and FIG. 5, the cooling water supplied by the tube 105 (FIG. 2) flows to the distal end side through a lumen 125 provided in the main unit 101. The members that cover the outside are not shown in FIG. 5.

A portion of the cooling water passes through an elliptical window 152 formed on one of the wall members 151 and flows into the inner space where the emitting part 112 moves, while the rest of the cooling water goes around the distal end. No other elliptical windows are formed on other wall member. After that, both flows are combined into one stream and will be returned through a lumen (not shown), which is provided for discharging the cooling water symmetrically to the lumen 125, and the tube 106.

The washing water supplied from a tube 141 (FIG. 2) flows through a lumen 142 and flows to the distal end, and bent toward the front window 145 by means of a flow passage 144 formed within the cap 143 to wash the outside of the light transmitting plate 148 provided at the front window 145. The proximal ends of the lumens 125, 142, etc., should be preferably provided with check valves in order to prevent the reverse flows of the cooling water and the washing water. A shared connecter (not shown) is provided and connected to the ends of the tubes 105, 106, and 141 together.

Figure 6:
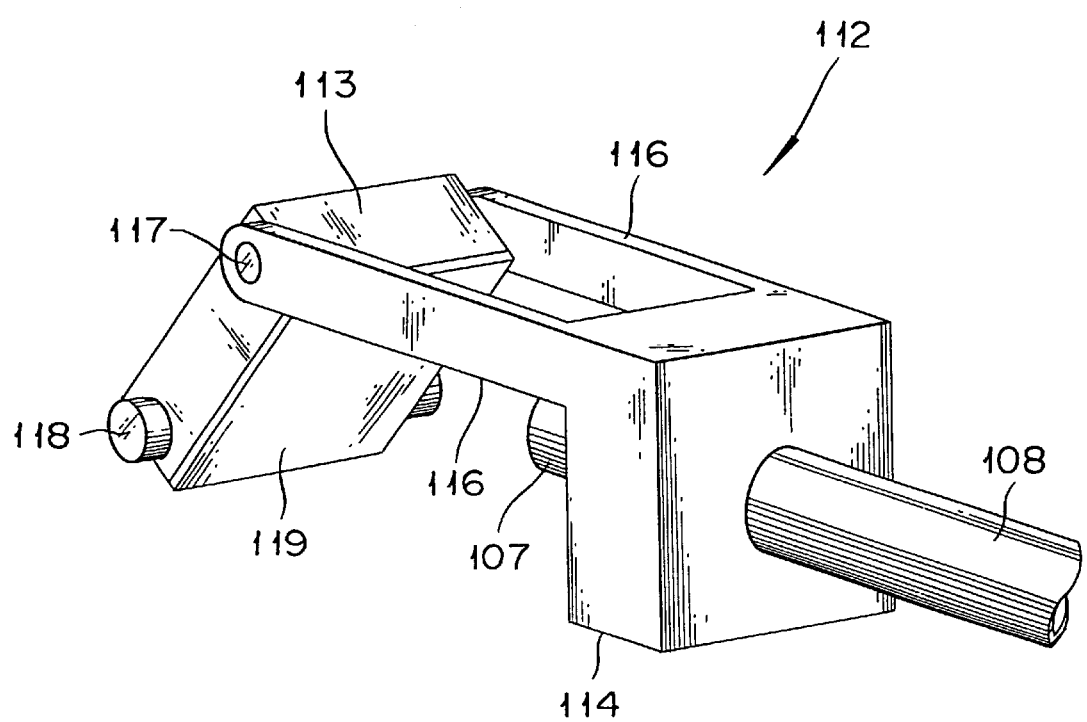
FIG. 6 is a perspective view of a laser beam emitting part connected to the distal end of an optical fiber in detail.

Next, the emitting part connected to the distal end of the optical fiber will be described with reference to FIG. 6.

The emitting part 112 is equipped with a fixed part 114 and a reflecting part 113 of the laser beam (energy). The fixed part 114 is fixed to the vicinity of the optical fiber 107, and the reflecting part 113 is connected to a pair of arms 116 extending from the left and right sides of the fixed part 114 to be able to rotate around a hinge shaft 117. Since the optical fiber 107 and the emitting part 112 moves together, the relative position of the tip of the optical fiber 107 against the reflecting part 113 remains approximately unchanged. In other words, the spot diameter of the laser beam remains stable without having to use any special optical system. Hence, the apparatus has a simpler structure, can be manufactured easily, and is less likely to develop trouble.

The reflecting part 113 has a flat surface 119 for reflecting the laser beam emitted by the optical fiber 107. The fixed part 114 is made to slide between a pair of wall members 151 in the main unit 101. At both sides of the distal end of the reflecting part 113 provided are pins 118 that match slidably with guide grooves 153 formed on the wall members 151.

The guide groove 153 includes a slide part 153*a*, a connection part 153*c*, and an extension part 153*b* as shown in FIG. 3. The slide part 153*a* is not parallel to the longitudinal direction of the main unit 101, is further away from the side window 150 on the proximal end side, and is closer to the side window 150 on the distal end side. The slide part 153*a* is formed within the range necessary for the reciprocating motion of the reflecting part 113. Generally, the connection part 153*c* is formed in an S-shape connecting between the slide part 153*a* and the extension part 153*b*. The extension part 153*b* is formed to extend from the connection part 153*c* to the proximal end.

The laser beam passages when the reflecting part 113 is located at a distal position P1, a middle position P2, and a proximal position P3 are described with reference to FIG. 7.

When the reflecting part 113 is located at the distal position P1, it rises up almost perpendicular to the longitudinal direction of the main unit 101 and reflects the laser beam at a small reflection angle. When the reflecting part 113 is located at the proximal position P3, it tilts down almost parallel to the longitudinal direction of the main unit 101 and reflects the laser beam at a large reflection angle. Therefore, when the reflecting part 113 makes a reciprocating motion while changing the tilt angle, the emitting position of the laser beam constantly moves but the axis of the laser beam is always aligned with a target region 121 in a tissue 120.

Next, the behavior of the reflecting part 113 during the laser beam irradiation and during the front observation will be described below.

As shown in FIG. 8, the reflecting part 113 is engaged with the slide parts 153*a* of the guide grooves 153 during the laser beam irradiation. On the other hand, as shown in FIG. 9, the reflecting part 113 engages with the extension parts 153*b* of the guide grooves 153 during the front observation by the endoscope 124. Consequently, the reflecting part 113 will be further tilted compared to the case when it is engaged with the slide parts 153*a* into a direction along the axis of the main unit 101, i.e., retracted into an approximately horizontal direction. Thus, the tip of the endoscope 124 can be pushed into a receiving cavity 146 formed near the distal end of the main unit 101 so as to have a better front view. As the connection parts 153*c* are formed into the approximately S-shape, it is possible to guide the reflecting part 113 into the extension parts 153*b* within a small stroke to tilt it into an approximately horizontal position.

Next, the proximal unit 50 and the insertion part 10 will be described.

Figure 10:
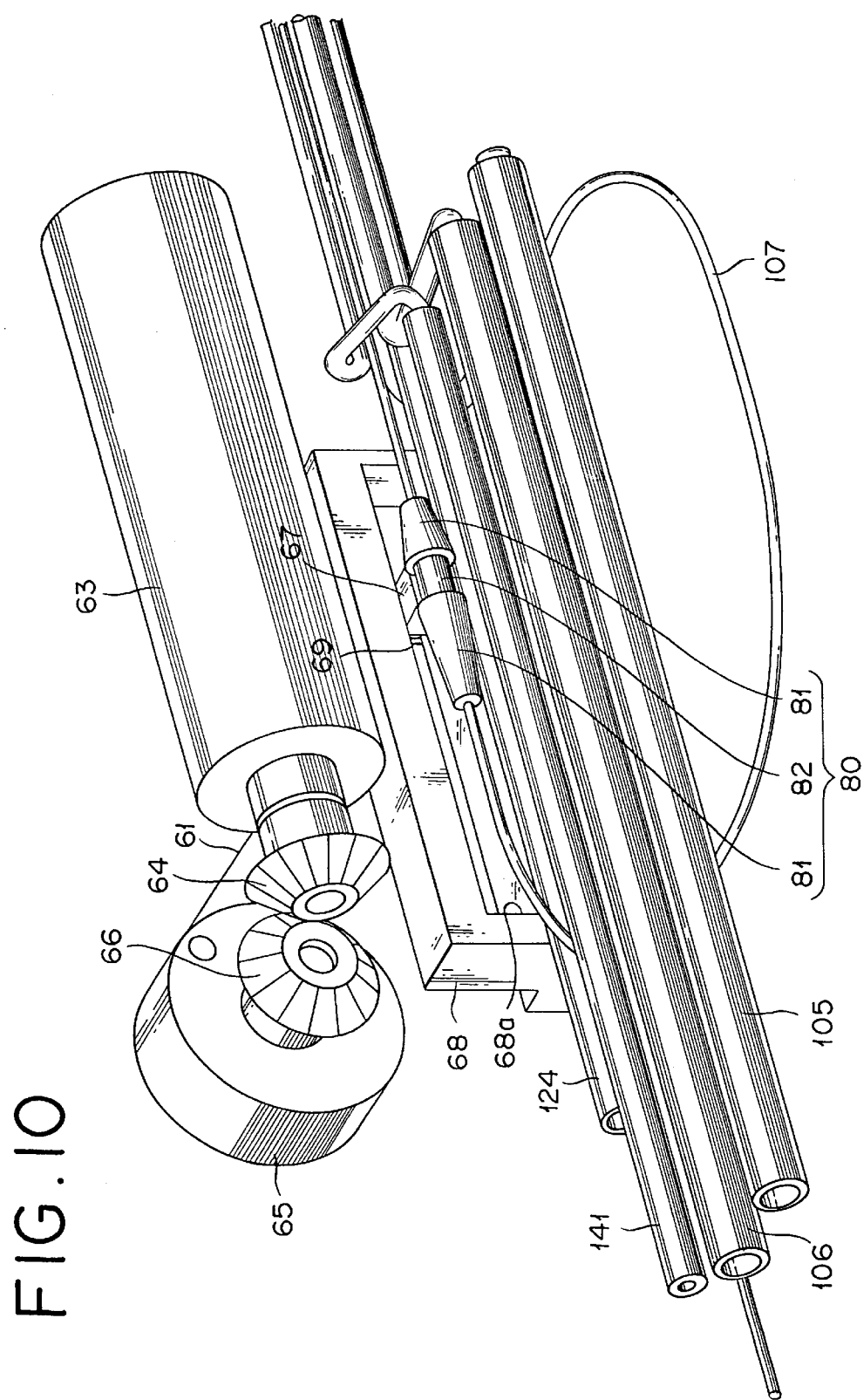
FIG. 10 is a perspective view of the internal structure in outline when an insertion part is fitted on a proximal unit.
Figure 11:
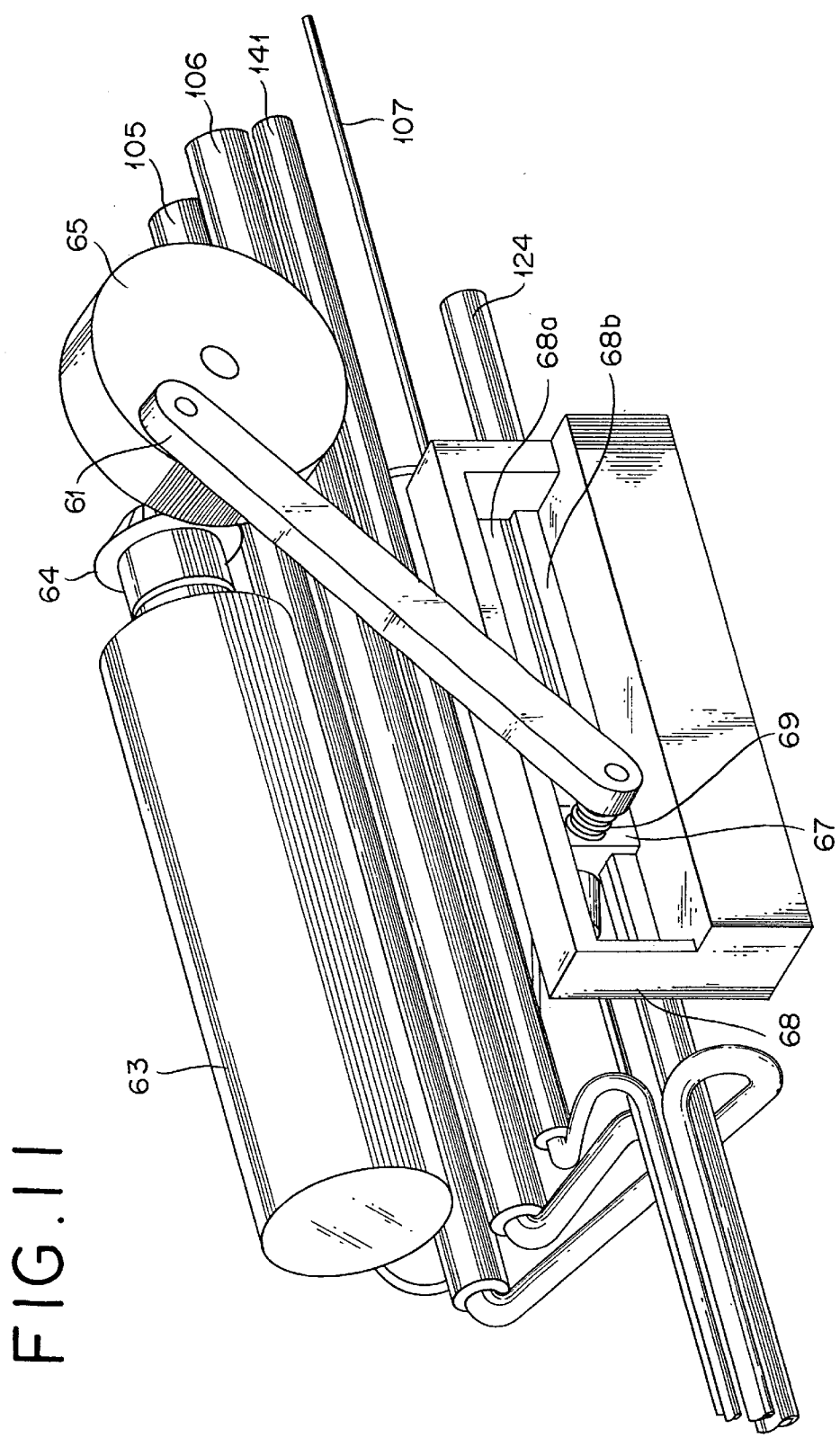
FIG. 11 is a perspective view of the apparatus from the left rear side of FIG. 10.

The insertion part 10 and the proximal unit 50 are constituted to be removable as described before. As shown in FIG. 10 and FIG. 11, the proximal unit 50 is provided with a motor (drive unit) 63. A bevel gear 64 provided on the drive shaft of the motor 63 is in mesh with a bevel gear 66 provided on a cam 65. The cam 65 is connected to a hook 67 via a linking mechanism 61. Therefore, when the motor 63 is driven, the drive force is transmitted to the hook 67 through the bevel gears 64 and 66, the cam 65 and the linking mechanism 61 to cause the hook 67 to make a reciprocating motion within a groove 68*a* of a guide member 68.

The hook 67 is provided with a compression spring 69, and is urged toward the insertion part 10 to be able to engage with an engaging member 80 fixed on the optical fiber 107. The hook 67 is restricted from moving toward the insertion part 10 by means of a stopper 68*b* of the guide member 68.

Figure 12:
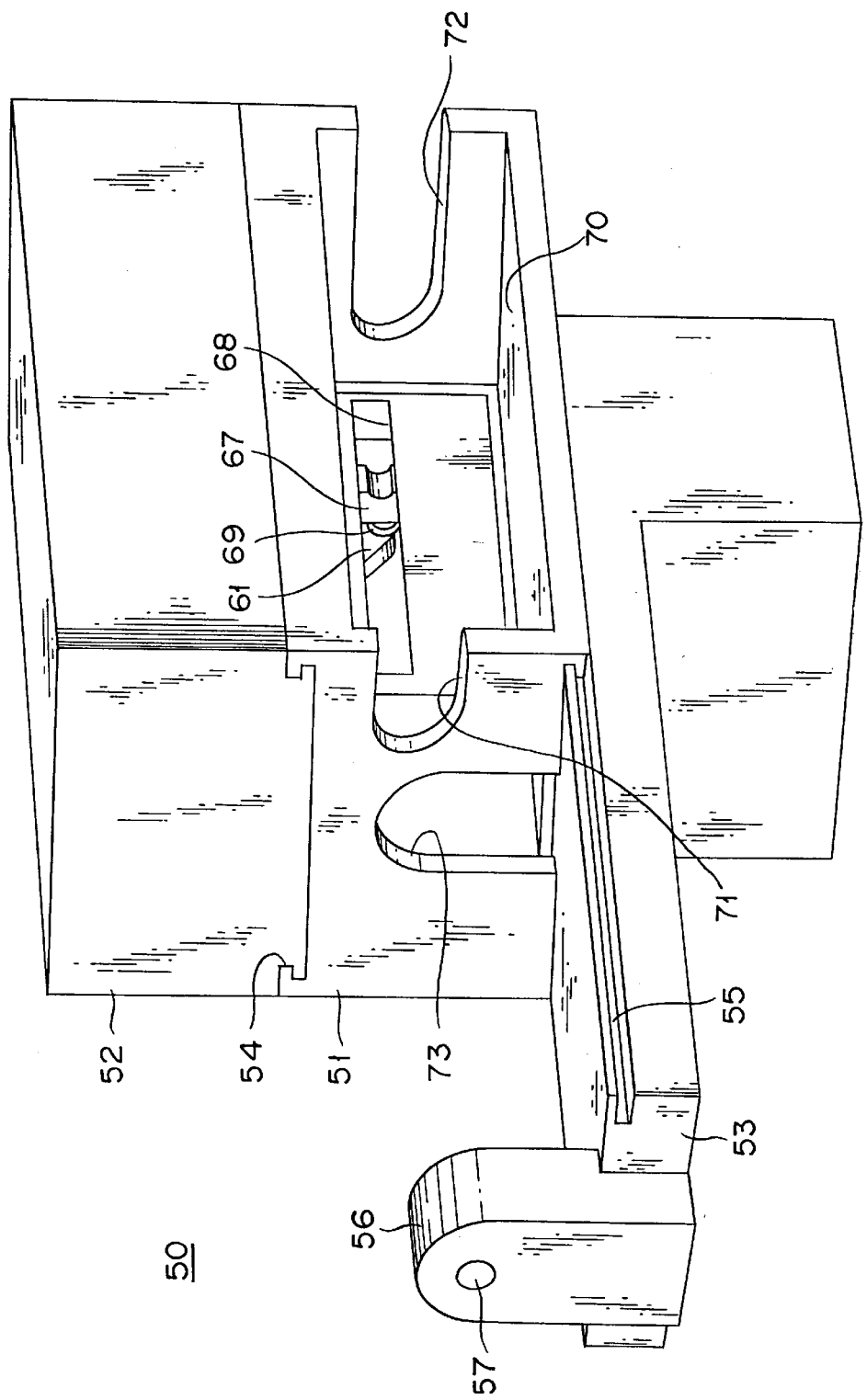
FIG. 12 is a perspective view of the proximal unit.

As shown in FIG. 12, the proximal unit 50 includes a mounting part 51, on which the insertion part 10 is directly mounted, an operating part 52 of the reflecting part 113, which is disposed slidably on the top portion of the mounting part 51 via a groove engagement part 54, and an operating part 53 of the endoscope, which is mounted on the bottom portion of the mounting part 51 via a groove engagement part 55.

The mounting part 51 has an insertion opening 70, into which the insertion part 10 is inserted. A groove 71, into which tubes and the like of the insertion part 10 are to be inserted, is formed on one side of the mounting part 51, and a groove 72, into which the main unit 101 of the insertion part 10 is to be inserted, is formed on the other side of the mounting part 51. Moreover, an insertion part 73, into which an endoscope 124 is to be inserted, is formed on one side of the mounting part 51.

The operating part 52 of the reflecting part 113 has the motor 63, the bevel gears 64 and 66, and the cam 65. The linking mechanism 61 connected to the cam 65 extends inside the mounting part 51. The hook 67 provided at the distal end of the linking mechanism 61 engages with the groove 68a of the guide member 68 provided at the mounting part 51. Therefore, by sliding the operating part 52 relative to the mounting part 51, the reflecting part 113 provided at the distal end of the optical fiber 107 can be moved in the longitudinal direction of the main unit 101 via the hook 67 and the engaging member 80 fixed on the optical fiber 107.

A supporting part 56 is provided at the rear end of the operating part 53 for supporting the endoscope 124. The endoscope 124 passes through a hole 57 formed on the supporting part 56 to be inserted into the main unit 101 and fixed to the supporting part 56 by means of a fixing part (not shown). Therefore, it is possible to slide the endoscope 124 along the longitudinal direction of the main unit 101 by moving the operating part 53 relative to the mounting part 51.

A linking mechanism is provided at the proximal unit 50 to move the endoscope 124. Therefore, as shown in FIG. 13A through FIG. 13C, while the endoscope 124 retracts toward the proximal end of the main unit 101 as the pins 118 of the reflecting part 113 move from the extension parts 153b toward the slide parts 153a, the endoscope 124 moves toward the distal end of the main unit 101 as the pins 118 of the reflecting part 113 move from the slide parts 153a toward the extension parts 153b.

Said linking mechanism has a lever 86 mounted rotatably on a pin 85 provided on the mounting part 51. Pins 87 and 88 provided on both ends of the lever 86 engage with a grove 89 formed on the operating part 52 of the reflecting part 113 and a groove 90 formed on the operating part 53 of the endoscope 124 respectively.

Figure 13A:
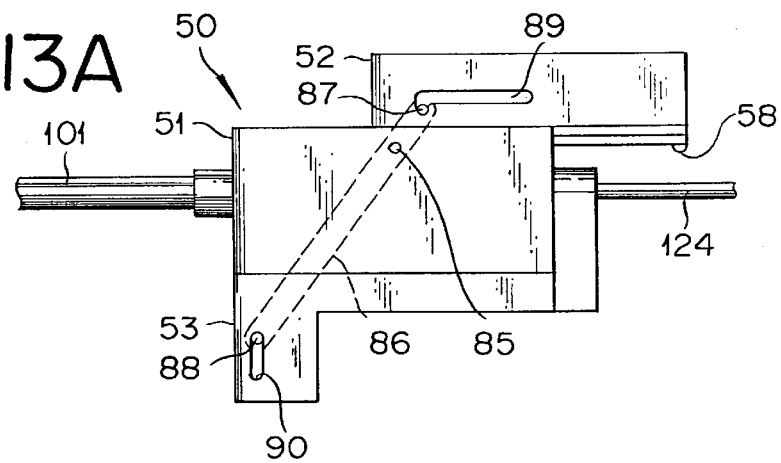
FIG. 13A through FIG. 13C are side views of assistance in explaining the linking mechanism between an operating part of the reflecting part and an operating part of an endoscope in the proximal unit.
Figure 13B:
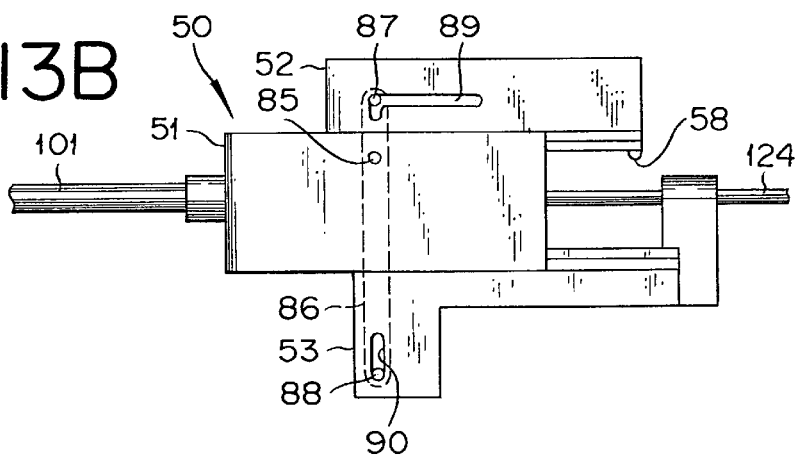
Figure 13C:
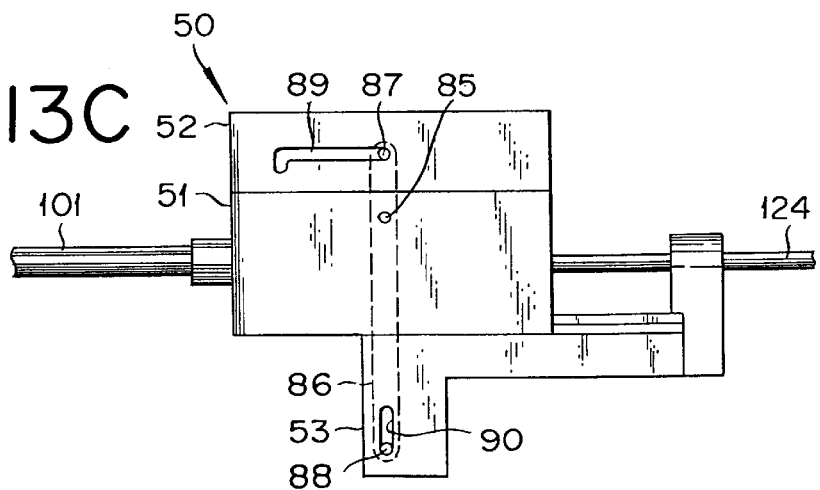

Therefore, as shown in FIG. 13A, when the operating part 52 is pulled back (rightward in FIG. 13A through FIG. 13C), the operating part 53 connected to the pin 88 on the opposite side of the lever 86 moves forward (leftward in FIG. 13A through FIG. 13C). On the other hand, when the operating part 52 is pushed forward, the operating part 53 moves back as shown in FIGS. 13B and 13C. It is possible to make the forward movement of the operating part 52 easier by means of applying an urging force to the lever 86 to rotate counterclockwise in FIG. 13A through FIG. 13C by providing a spring.

Furthermore, a bush type switch 58 is provided at the dead end of the proximal side of the slide surface of the mounting part 51 in order to prevent error motions. More specifically, the motor 63 rotates only when the switch 58 is pressed as the operating part 52 and the mounting part 51 becomes united as shown in FIG. 13C to cause the current to be supplied to the motor 63. The switch 58 can be replaced with various sensors.

Figure 14:
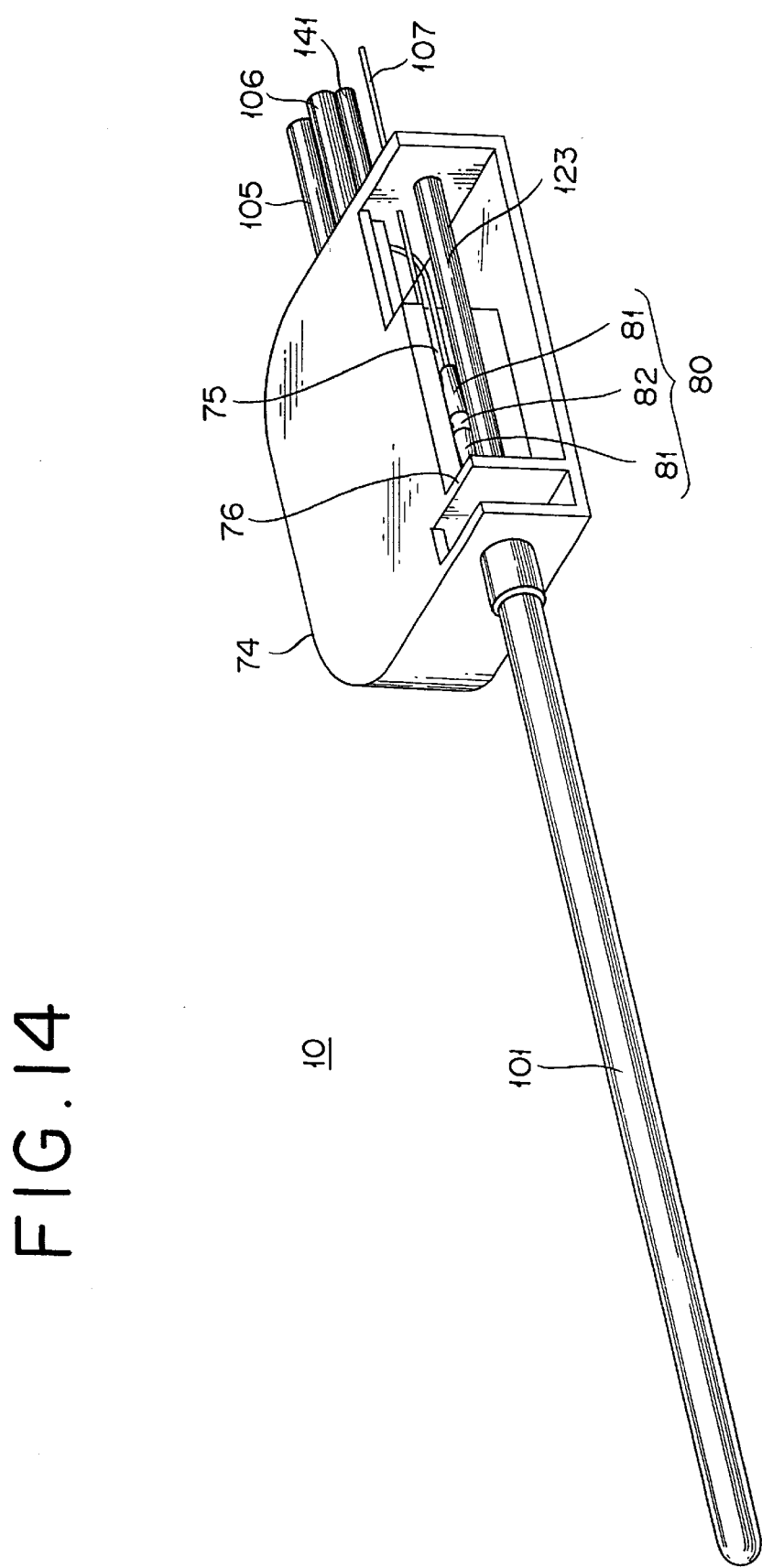
FIG. 14 is a perspective view of the insertion part.

As shown in FIG. 14, the insertion part 10 has a proximal unit 74 where the main unit 101 is connected. The proximal unit 74 is mounted with the tube 105 for supplying the cooling water, the tube 106 for discharging the cooling water, the tube 141 for supplying the washing water, the lumen 123 for the endoscope, and the optical fiber 107.

The optical fiber 107 is attached with the engaging member 80 for engaging the hook 67. The engaging member 80 includes a pair of taper parts 81, 81 as the guide parts formed to be tapered and an indented narrow part 82 between them. The proximal unit 74 of the insertion part 10 is provided with a guide surface 75 as the supporting part for supporting the engaging member 80 slidably in the lengthwise direction of the main unit 101, and a restricting plate 76 that restricts the forward movement of the engaging member 80.

Thus, the hook 67 which makes a reciprocating motion driven by the motor 63 goes over the taper part 81 and engages automatically with the narrow part 82 of the engaging member 80 as the engaging member 80 is stopped pressing against the restricting plate 76. It is necessary to keep the engaging member 80 on the side of the restricting plate 76 in advance, so that it can abut with the restricting plate 76 and stop as a result of the reciprocating motion of the hook 67.

When irradiating the laser beam by causing the optical fiber 107 to reciprocate, the reciprocating motion of the hook 67 driven by the motor 63 is securely transmitted to the optical fiber 107 via the fitting structure between the hook 67 and the narrow part 82.

The optical fiber 107 is stored in the proximal unit 74 of the insertion part 10 in a loop form as shown in FIG. 10 and FIG. 14. The looped portion serves as a reserve for the reciprocating motion when the optical fiber 107 reciprocates.

Next, the actual use condition and action of the apparatus 100 will be described.

In order to use the apparatus 100, the proximal unit 74 of the insertion part 10 is inserted into the insertion opening 70 formed on the mounting part 51 of the proximal unit 50. Then, the hook 67 is caused to reciprocate by means of the motor 63 within the proximal unit 50. Thus, the hook 67 goes over the taper part 81 of the engaging member 80 provided on the optical fiber 107 and engages with the narrow part 82 of the engaging member 80 automatically. Consequently, the hook 67 on the side of the proximal unit 50 becomes solidly fixed to the engaging member 80 provided on the optical fiber 107 on the side of the insertion part 10.

Because of such a fitting structure between the hook 67 and the narrow part 82, it is possible to transmit the reciprocating drive power by the motor 63 securely to the optical fiber 107 by installing the insertion part 10 in the proximal unit 50 easily and securely. As a result, the proximal unit 50, which contains the motor 63 etc. and is relatively expensive to manufacture, can be reused, while the insertion part 10, which includes the optical fiber 107, other plastic components, etc. and is relatively inexpensive to manufacture, can be discarded after the use and can be replaced easily.

The insertion part 10 provided with the main unit 101, on which the emitting part 112 is disposed, is always new, so that it is easy to maintain the function and performance of the apparatus easily. Moreover, since the insertion part 10, which is inserted into the human body during the treatment, is discarded after the use, the labor of disinfection process to eliminate the possibility of infections of diseases due to the reuse of the unit can be eliminated.

In addition, even if the hook 67 is not accurately positioned in loading the insertion part 10 into the proximal unit 50, the hook 67 makes a reciprocating motion to fit with the narrow part 82 automatically. Therefore, it is possible to use a relatively inexpensive small motor instead of an expensive motor with a better positioning accuracy, to make the proximal unit 50 smaller and lighter, and to improve the operating capability of the apparatus 100.

Figure 7:
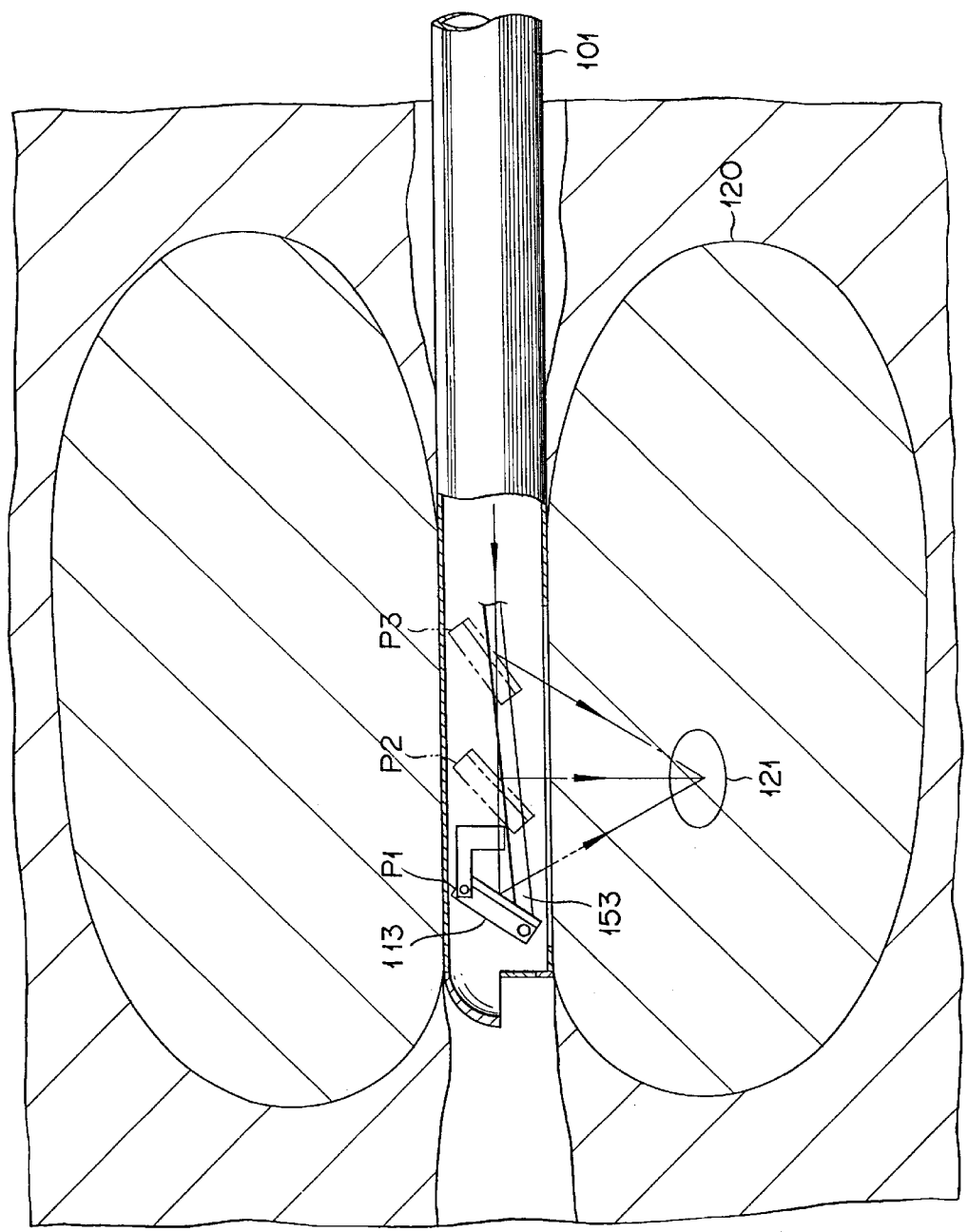
FIG. 7 is a schematic illustration of assistance in explaining the passage of the laser beam when a reflecting part is at a distal position, a middle position and a proximal position during its reciprocating motion.

In the treatment of benign prostatic hyperplasia, as shown in FIG. 7, the main unit 101 is inserted into the urethra and its distal end is positioned in the vicinity of the target region 121 of the tissue 120, which is the lesional region, i.e., the prostatic tissue. During the positioning, it is desirable to confirm the position of the distal end of the main unit 101 directly using the endoscope 124.

At this time, the operating part 52 of the reflecting part 113 is pulled backward and the operating part 53 of the endoscope 124 is moved forward as shown in FIG. 13A. This way, as the pins 118 of the reflecting part 113 move from the slide parts 153a to the extension parts 153b, the endoscope 124 moves toward the distal end of the main unit 101.

By causing the reflecting part 113 to engage with the extension parts 153b by means of the operating parts 52 and 53 and to tilt in such a way as to be approximately parallel with the axis of the main unit 101, it becomes possible to cause it to retract. Consequently, the endoscope 124 will not only have a front view unhindered by the reflecting part 113, but also the distal end of the endoscope 124 can move deeper into the distal end of the main unit 101 without hindered by the reflecting part 113. Thus, it becomes possible to have a more detailed observation of the frontal area of the insertion direction of the main unit 101 (FIG. 9), and allows a more accurate positioning of the distal end of the main unit 101 inside the human body.

It is also possible to use an endoscope with a larger diameter to provide a clearer and wider field of view even within the main unit 101 of the limited diameter. Hence, it is possible to position the distal end of the main unit 101 more accurately and observe the tissue surface during the laser irradiation more smoothly to accomplish a more accurate laser beam irradiation and reduce the burden of the patient by reducing the treatment time.

Furthermore, since it uses a linking mechanism that makes the axial motions of the reflecting part 113 and the endoscope 124 opposite to each other with respect to the movement toward the distal end of the main unit 101, it securely prevents the possibility of the reflecting part 113 and the endoscope 124 accidentally interfering with each other.

It is possible to execute the adjustment of the position of the distal end of the main unit 101 provided with the emitting part 112 relative to the target region 121 by means of observing the tissue surface layer by means of the endoscope 124 through the front window 145 and the side window 150 and moving the entire apparatus 100 in a specified direction (longitudinal direction of the main unit 101) or rotating the entire apparatus 100 manually.

Next, the cooling water is circulated inside the apparatus 100 by operating the cooling water circulating apparatus. More specifically, the cooling water flows into the distal end of the main unit 101 through the tube 105 and the lumen 125 and cools various components heated by the laser beam and the surface of the tissue contacting the cover 104.

After the above operations are completed, the operating part 52 of the reflecting part 113 is pressed forward as shown in FIG. 13B and FIG. 13C and the operating part 53 of the endoscope 124 is retracted. As a result, when the pins 118 of the reflecting part 113 move from the extension parts 153b to the slide parts 153a, the endoscope 124 moves back from the distal end of the main unit 101. After the endoscope 124 has moved back by a sufficient amount, and the reflecting part 113 has passed through the condition of its engagement with the extension parts 153b (FIG. 13B), the operating part 52 is pressed forward to cause the reflecting part 113 engage with the slide parts 153a (FIG. 13C and FIG. 8).

After the motor 63 has been started, the laser beam generator is operated. The laser beam generated by the laser beam generator is guided into the emitting part 112 through the optical fiber 107. The laser beam is then reflected sideway by the reflecting part 113, and is directed to the target region 121 through the side window 150. At that time, the reflecting part 113 changes its direction of reflection while making a reciprocating movement at a frequency of 0.1–10 Hz in the axial direction in such a way that all beams cross at the target region 121 although the laser beam axis varies continuously.

The irradiated laser beam heats the target region 121 inside the tissue 120 and its vicinity to a desired temperature. In the meantime, the amount of laser beam irradiation at an arbitrary point in the area above the target region 121 in FIG. 7, i.e., the area closer to the apparatus 100, e.g., the surface layer of the tissue 120, is small so that only a small amount of heat is generated.

Similarly, the amount of laser beam irradiation is small at the area far from the target region 121 in FIG. 7 so that only a small amount of heat is generated. Therefore, the areas surrounding the target region 121 are maintained at relatively low temperatures and are protected from the effects of laser beams.

Next, laser beams will irradiate a different target region 121. By repeating this process, multiple regions of treatment can be heated.

As can be seen from the above description, the medical energy irradiation apparatus according to the first embodiment will make it possible to reuse the portion, which contains the motor, etc., and is relatively expensive to manufacture, while scrapping the portion including the long shaft-like main unit, which is relatively inexpensive to manufacture, each time it is used.

This result in always using a brand new main unit provided with the emitting part in each treatment, so that it is easy to achieve the equipment function and performance in top condition and reduce the patient's burden. Moreover, as the used main unit is discarded once it is used, the burden on the clinical staff based on reusing of the unit can be removed.

Although the shapes of the taper parts 81 formed on both sides of the narrow part 82 are in conical shapes in the first embodiment, they can be formed in a prismoid or a truncated circular cone split in half parallel by a plane parallel to the axis.

Next, a laser beam irradiation apparatus according to the second embodiment will be described below. The descriptions will be concentrated on the differences from the first embodiment and common members will be indicated with the same symbols so that their descriptions do not have to be repeated.

Figure 15:
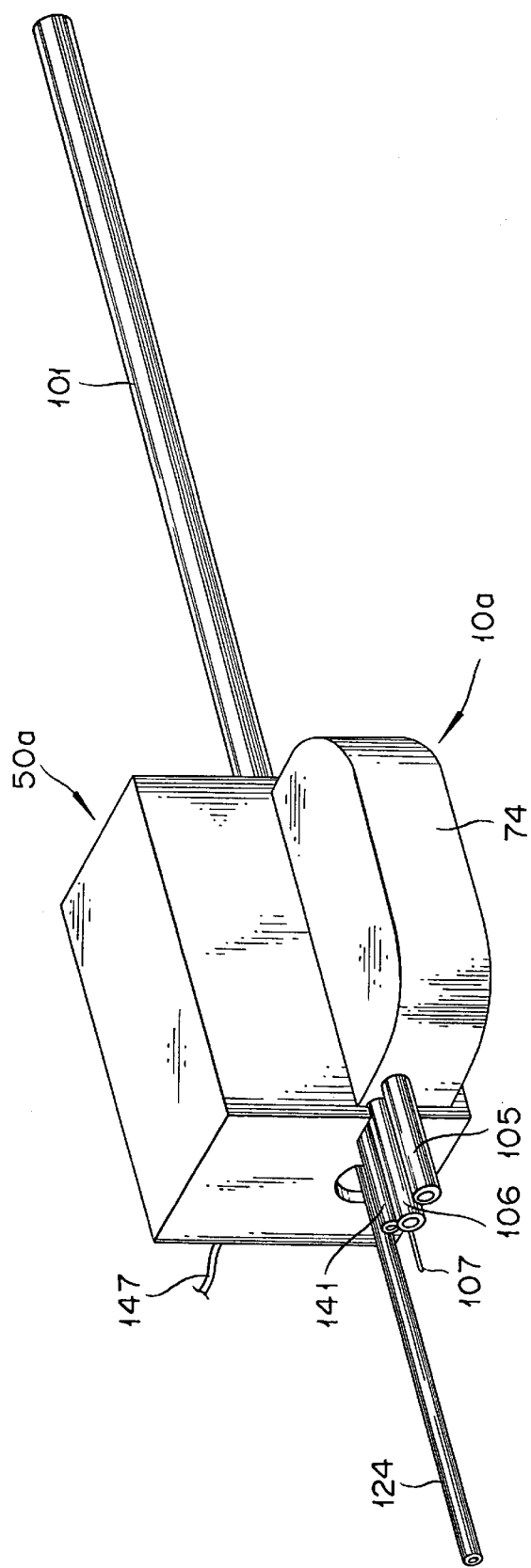
FIG. 15 is a perspective view of a laser beam irradiation apparatus according to the second embodiment of the invention.
Figure 16:
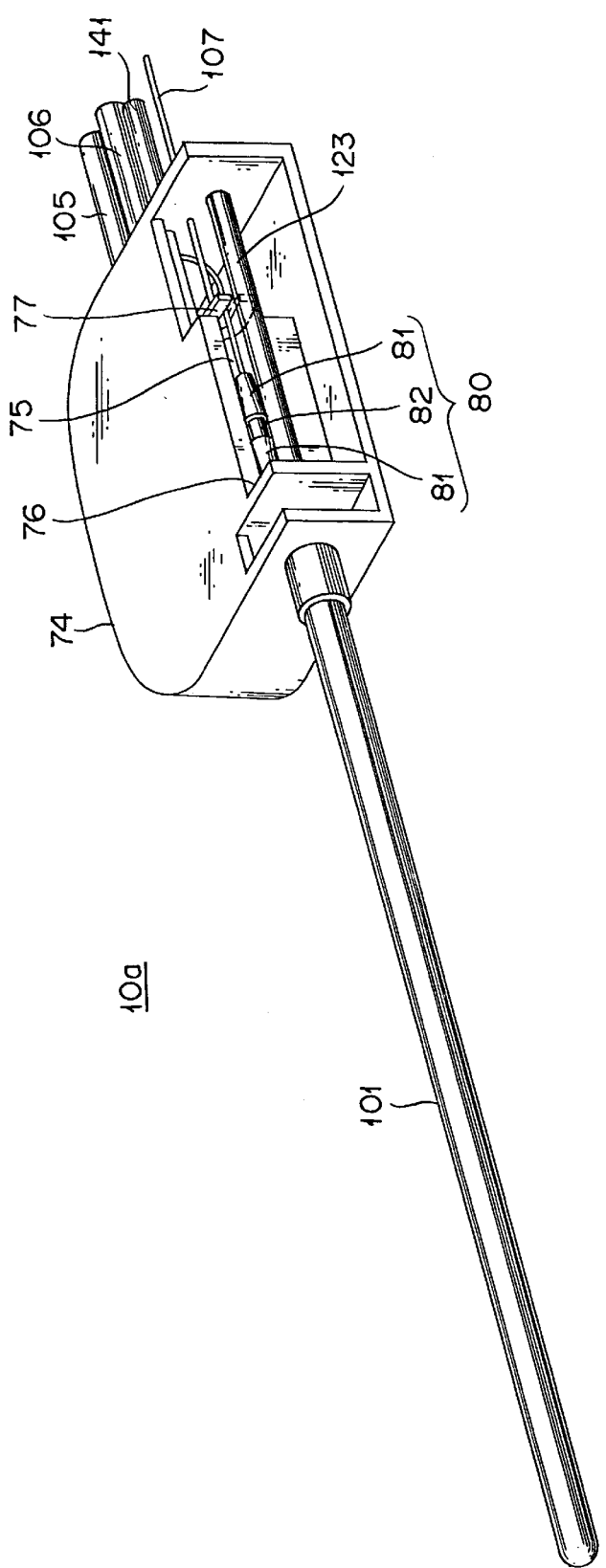
FIG. 16 is a perspective view of the insertion part shown in FIG. 15.

In the second embodiment, a proximal unit 50a has only one casing as shown in FIG. 15, and no operating part is provided for the user to operate to move the reflecting part 113 in the longitudinal direction of the main unit 101. Thus, the constitution for retracting the reflecting part 113 in an engagement with the extension parts 153b is eliminated to form a simpler constitution as a whole. On the other hand, in addition to the restricting plate 76 that restricts the forward motion of the engaging member 80, an additional restricting plate 77 is provided to restrict the backward motion in the proximal unit 74 of an insertion part 10a as shown in FIG. 16.

When the motor 63 causes the hook 67 to reciprocate, the engaging member 80 will be pressed by the hook 67 and will be made to stop by either the restricting plate 76 or 77. Under this condition, the hook 67 goes over the taper part 81 and automatically engages with the narrow part 82 of the engaging member 80. In other words, when the engaging member 80 is located between the restricting plate 76 and the restricting plate 77, the hook 67 can be automatically engaged with the narrow part 82. This provides an advantage that it is not necessary to keep the engaging member 80 toward the side of either the restricting plate 76 or the restricting plate 77, for example, the side of the restricting plate 76 in advance, when installing the insertion part 10a on the proximal unit 50a.

As can be seen from the above description, the second embodiment has a constitution where the hook with a substantially U-shaped groove is guided by the guide part formed in the tapered shape to engage with the narrow part in the indented shape to make it possible for the first engaging member provided on the power transmission member to engage with the second engaging member to be easily disengaged when necessary. For example, the hook can automatically engage with the narrow part by simply causing the hook to reciprocate by the drive mechanism even if the hook is not precisely positioned. Therefore, it is possible to use an inexpensive small motor as a driving device of the drive mechanism, reduce the size and weight of the drive mechanism, and improve the maneuverability of the laser beam irradiation apparatus.

Next, the laser beam irradiation apparatus according to the third embodiment will be described with reference to FIG. 17A and FIG. 17B. The descriptions will be concentrated on the differences from the first and second embodiments and common members will be indicated with the same symbols so that their descriptions do not have to be repeated.

In the third embodiment, the proximal unit includes the mounting part 51 to which the insertion part 10 is directly mounted, and the operating part 52 of the reflecting part 113 that is slidably mounded on top of the mounting part 51 via a groove engaging part (not shown). In addition, the proximal unit is provided with a restricting member. The restricting member selectably allows either the engagement between the reflecting part 113 and the slide parts 153a of the guide grooves 153 or the movement of the main unit 101 of the endoscope 124 toward the distal end.

The restricting member has a lever 86a mounted rotatably on a pin 85a, which is provided on the mounting part 51. A pin 87a that engages with a groove (not shown) formed on the operating part 52 is provided on one end of the lever 86a, and an engaging groove 86b substantially formed in a U-shape seen from the axial direction of the endoscope 124 is formed on the other end of the lever 86a. A stepped part 124a, which can engage with the engaging groove 86b, is formed at a specific position on the outer circumference of the protective tube of the endoscope 124.

Figure 17A:
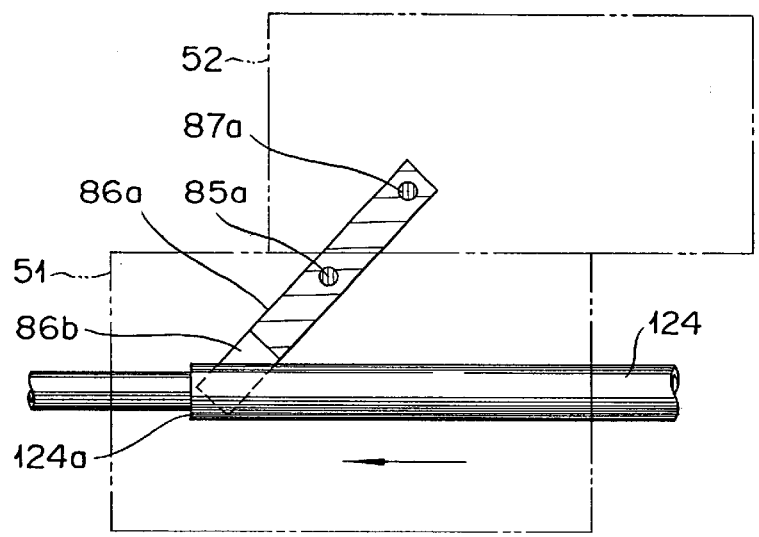
FIG. 17A and FIG. 17B are side views of a proximal unit according to the third embodiment of the invention.
Figure 17B:
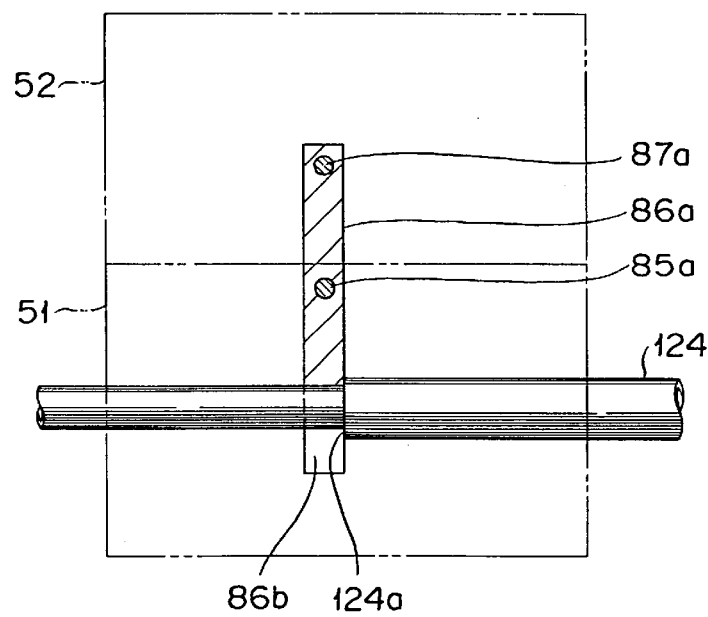
Figure 18:
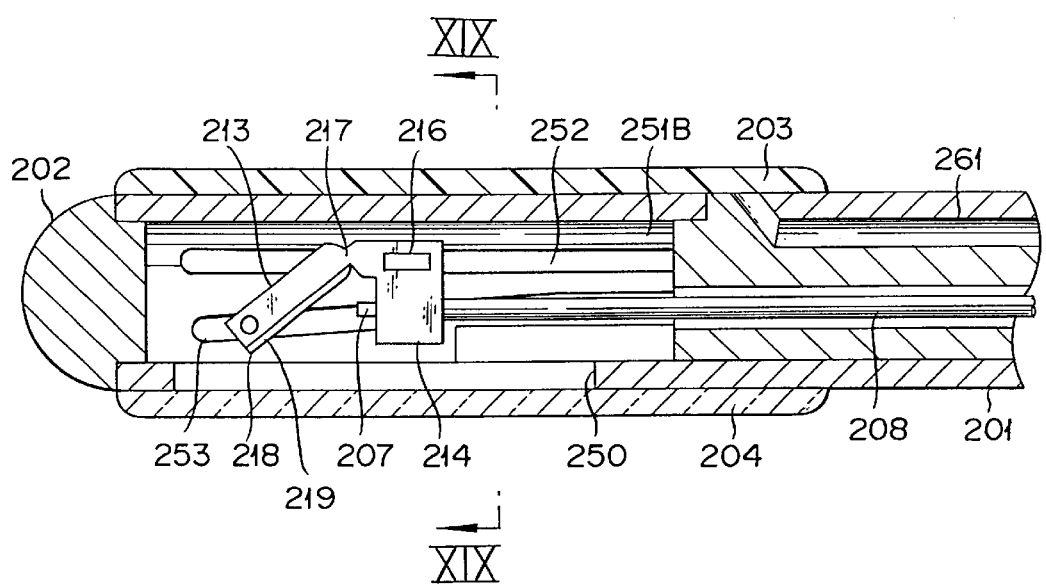
FIG. 18 is a cross section of assistance in explaining the constitution of the distal end of the main unit of a laser beam irradiation apparatus according to the fourth embodiment of the invention.
Figure 19:
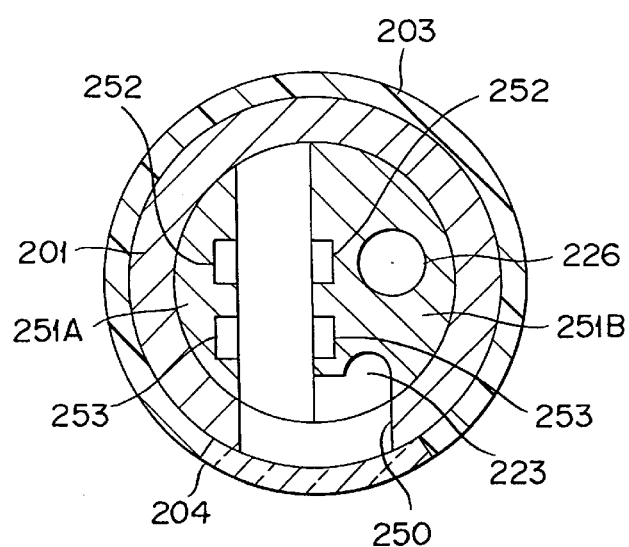
FIG. 19 is a cross section taken on line XIX—XIX line of FIG. 18.

Consequently, when the operating part 52 is pulled backward, the lever 86a tilts and the engaging groove 86b moves forward and up direction (FIG. 17A). As a result of the moving operation of the operating part 52, the reflecting part 113 is tilted into a substantially horizontal position in parallel with the axis of the main unit 101 and into a retracted position, while the endoscope 124 is simultaneously relieved from the restriction of the engaging groove 86b and allowed to move toward the distal end of the main unit 101 (the arrowed direction in the drawing). On the other hand, if the operating part 52 is pushed forward, the lever 86a rises up vertically and the engaging groove 86b moves toward the lowest end (FIG. 17B). With the moving operation of the operating part 52, the reflecting part 113 engages with the slide parts 153a of the guide grooves 153 and the endoscope 124 is restricted by the engaging groove 86b to be prohibited from moving toward the distal end of the main unit 101.

Thus, the restricting member is used to allow either the reflecting part 113 or the endoscope 124 to move only toward the distal end of the main unit, it can securely prevent the reflecting part 113 and the endoscope 124 from interfering with each other with a simple constitution.

According to the third embodiment described above, the laser beam (energy) reflecting part engages with the extension parts of the guide mechanism by means of the operating part, so that it further tilts toward a direction in parallel with the axis of the main unit, compared with the engagement with the slide parts, and into a retracted position. Therefore, not only the front view of the endoscope is not interfered by the reflecting part, but also the tip of the endoscope can be moved toward the inner part of the distal end of the main unit with no interference from the reflecting part so that it becomes possible to have a more detailed observation of the frontal area of the insertion direction of the main unit, and allows a more accurate positioning of the distal end of the main unit inside the human body.

It is also possible to use an endoscope with a larger diameter to provide a clearer and wider field of view even within the main unit of the limited diameter. Hence, it is possible to position the distal end of the main unit and observe the tissue surface during the laser irradiation more smoothly, and to accomplish a more accurate laser beam irradiation and reduce the burden of the patient by reducing the treatment time.

Furthermore, since it uses the linking mechanism that makes the axial motions of the reflecting part and the endoscope opposite to each other with respect to the movement toward the distal end of the main unit, or the restricting mechanism that allows either the reflecting part or the endoscope to move only toward the distal end of the main unit, it securely prevents the possibility of the reflecting part and the endoscope accidentally interfering with each other.

Although it was shown above that the extension part 153b of the guide groove 153 is located on the proximal side of the slide part 153a in the third embodiment, it can also be positioned on the distal side of the slide part 153a.

Next, a laser beam irradiation apparatus according to the fourth embodiment will be described in the following with reference to FIG. 18 through FIG. 24. The descriptions will be concentrated on the differences from the first through third embodiments and common members will be indicated with the same symbols so that their descriptions do not have to be repeated.

The fourth embodiment is particularly different from the other embodiment with respect to the construction of the emitting part connected to the tip of the optical fiber. Incidentally, moving parts are not shown in FIG. 19 for the sake of convenience of the description.

The distal end of a main unit 201 of a laser beam irradiation apparatus has a sealed tip and a window 250, which is an opening for transmitting laser beams. The tip of the main unit 201 has wall members 251 (251A, 251B) to define the internal space of the distal end. Guide grooves 252 and 253 are formed on the wall member 251.

A light transmitting cover 204 is fixed to the surface of the main unit 201 by adhesion in order to protect the window 250. A balloon 203 is placed to cover the area except the cover 204 and the widow 250 through which the laser beam is transmitted. The balloon 203 is made of a thin plastic film with elasticity and is inflated by liquid poured through a lumen 261 to press the side where the window 250 exists against the surface of the tissue.

An optical fiber 207 for transmitting the laser beam is located inside the main unit 201. The optical fiber 207 is covered by a protective pipe 208 made of stainless steel except the area located in the internal space of the distal end of the main unit 201 in order to protect it from damages or bending. The proximal end of the optical fiber 207 is connected to a laser beam generator via an optical connector.

Next, the side emitting mechanism of the laser beam is described.

Figure 20:
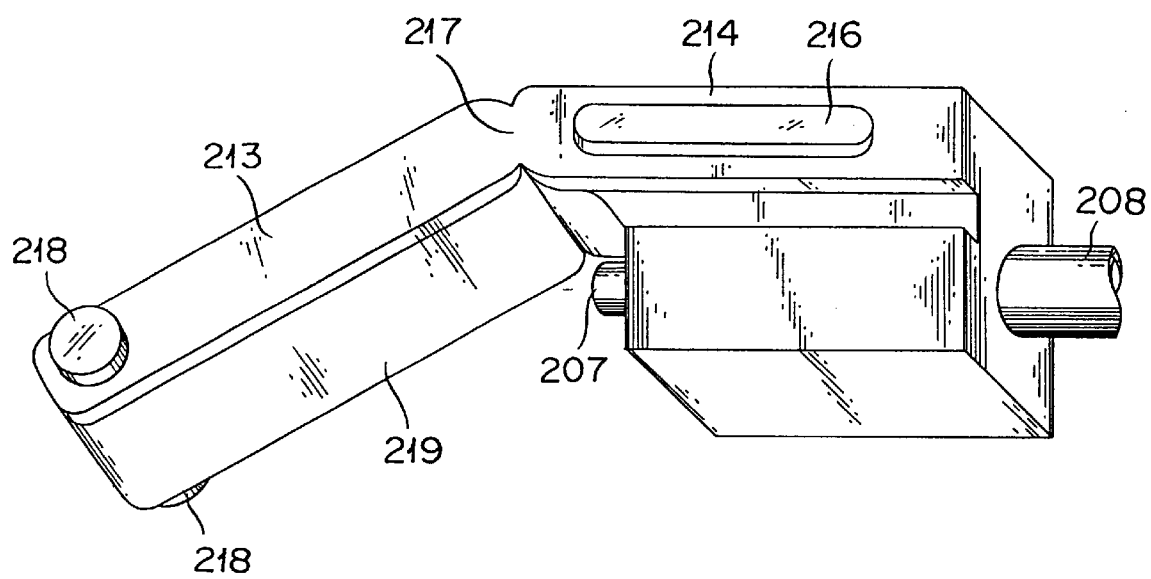
FIG. 20 is a perspective view of a laser beam emitting part.

The emitting part has a reflecting part 213, a fixed part 214, and a flexing part 217 located between the fixed part 214 and the reflecting part 213 as shown in FIG. 20. The reflecting part 213 has protrusions 218 formed on the side surfaces, and a flat surface 219 for reflecting sideways the laser beams radiated from the tip of the optical fiber 207.

The protrusion 218 fits slidably into the guide groove 253 provided on the wall member 251 at the distal end of the main unit 201. The guide groove 253 is not parallel to the axial direction of the main unit 201 except the proximal end. The distance between the guide groove 253 and the axis of the main unit 201 expands from the proximal to its distal end.

Its distal end is located outside of the reciprocating range of the reflecting part 213, the length is several millimeters, and it s parallel to the axial direction of the main unit 201. The parallel portion is provided for making it easier to insert each moving part into the distal end of the main unit 201 during manufacturing. The protrusions 218 and the guide grooves 253 have an angle changing mechanism for changing the reflecting angle of the flat surface 219.

The fixed part 214 is fixed on the optical fiber 207 (protective pipe 208). Consequently, the positional relation between the reflecting part 213 and the distal end of the optical fiber 207 is maintained approximately constant as the emitting part makes a reciprocating motion with the optical fiber 207. Therefore, it is possible to stabilize the spot diameter of the laser beam without using a special optical system. Moreover, the fixed part 214 has protrusions 216 formed on both sides. The protrusions 216 fit slidably with the guide grooves 252 provided on the wall members 251 to stabilize the reciprocating motion of the emitting part. Thus, the protrusions 216 and the guide grooves 252 are for the stabilization of the straight stroke and are provided as needed.

The flexing part 217 is made to flex repetitively by means of the angle changing mechanism as the emitting part reciprocates in order to change the reflecting angle of the flat surface 219. Since the emitting part does not need a hinge mechanism to make the reflecting angle of the flat surface 219 variable, it is easier to manufacture and less likely to cause troubles as its structure is simple. The flexing part 217 is preferably made by forming together with the reflecting part 213 and the fixed part 214 in one piece by means of the injection molding method such as two color forming or insert forming. In other words, it is preferable that the emitting part be made as an integral unit.

The flexing part 217 is made of a material having an excellent flexing characteristic. The preferable materials for this purpose include rubber and plastic materials such as polystyrene, polyurethane, polyvinyl chloride, polypropylene, and polyethylene, more preferably, polypropylene and polyethylene.

The flexing part 217 has a groove on the first surface located on the side of the flat surface 219 in order to make flexing easier. The flexing part 217 is made to flex repetitively around the groove. However, it is possible to make the flexing easier by means of making the thickness of the flexing part 217 thinner than the thickness of the reflecting part 213 and the fixed part 214, or forming a hole in the flexing part 217. The groove on the first surface has an edge formed on the bottom to make the flexing part 217 flexes more accurately.

The flexing part 217 further has a groove having an edge formed on its bottom on the second surface, which is located on the opposite side of the first surface in order to make the flexing easier. The groove of the second surface can have a cross section consisting of curves without any edges.

In addition, the first distance between the tip of the edge of the first surface and the fixed part is made longer than the second distance between the tip of the edge of the second surface and the fixed part.

Figure 21A:
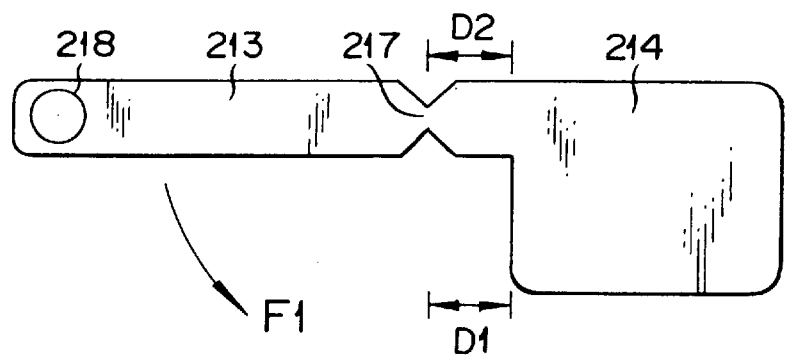
FIG. 21A through FIG. 21C are schematic illustrations of assistance in explaining the force to flex a flexing part of the emitting part.
Figure 21B:
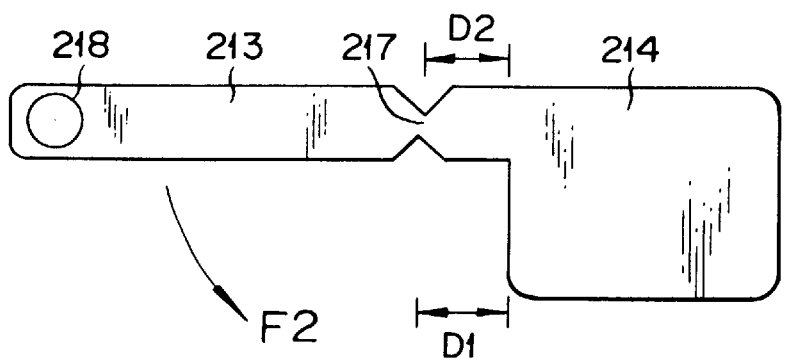
Figure 21C:
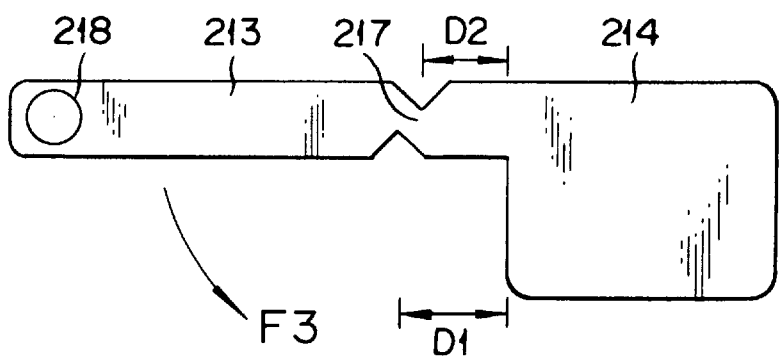

The force F2 for flexing the flexing part 217, when the first distance D1 is longer than the second distance D2 as shown in FIG. 21B, is smaller than the force F1 for flexing the flexing part 217, when the first distance D1 is equal to the second distance D2 as shown in FIG. 21A. When the difference between the first distance D1 and the second distance D2 is larger that the same in FIG. 21B, the force F3 for flexing the flexing part 217 as shown in FIG. 21C is smaller than the force F2 in FIG. 21B.

Figure 22:
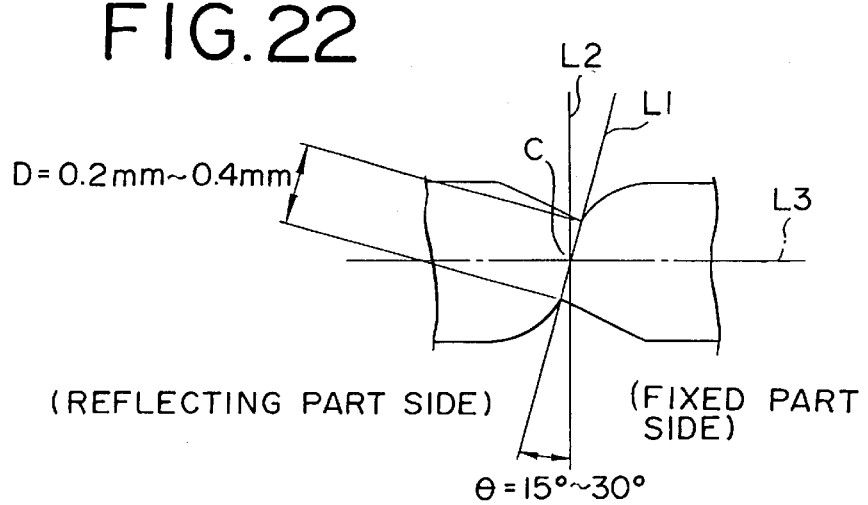
FIG. 22 is an enlarged view of the flexing part.

FIG. 22 shows a preferable difference between the first distance and the second distance from the standpoint of the cross angle__. The cross angle__is an angle formed between a line L1 that connects the tip of the edge of the first surface and the tip of the edge of the second surface and a perpendicular line L2 to the centerline L3 of the flexing part 217. As shown in the drawing, the cross angle__is preferably 15 to 30 degrees. The point C, where the line L1, L2 and L3 cross together, is the center of the repetitive flexing. The distance between the tip of the edge of the first surface and the tip of the edge of the second surface, i.e., the thickness is preferably 0.2 to 0.4 mm.

Figures 23A, 23B, 23C:
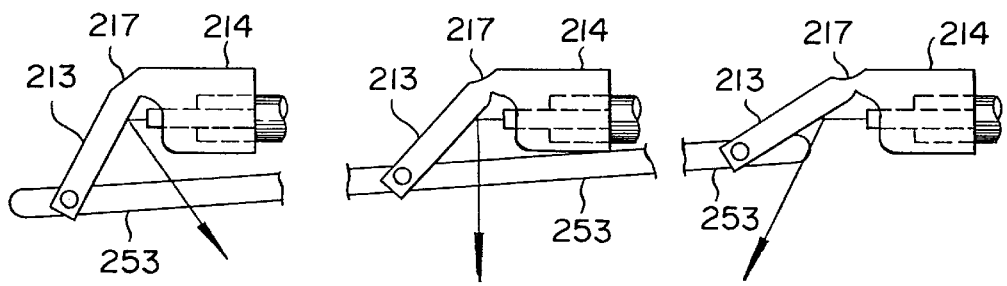
FIG. 23A through FIG. 23C are schematic illustrations of assistance in explaining how a reflecting part reciprocates while changing a reflection angle.

With the above constitution, the reflecting part 213 rises up approximately vertical to the axis direction of the main unit 201 as shown in FIG. 23A when it is located at the tip position corresponding to the flexing angle of 60 degrees. Therefore, the sum of the incident angle of the laser beam and the reflecting angle is less than 90 degrees. On the other hand, when it is located at the proximal position corresponding to the flexing angle of 30 degrees as shown in FIG. 23C, the reflecting part 213 tilts almost to a direction parallel to the axial direction of the main unit 201. Therefore, the sum of the incident angle of the laser beam and the reflecting angle becomes greater than 90 degrees. Moreover, if the reflecting part 213 is located in the intermediate position corresponding to the flexing angle of 45 degrees, the sum of the incident angle of the laser beam and the reflecting angle becomes 90 degrees as shown in FIG. 23B. Therefore, when the reflecting part 213 makes a reciprocating motion while changing the reflecting angle, the emitting position of the laser beam constantly moves but the axis of the laser beam is always aligned with a target region 221. The flexing angle is the angle formed between the axis of the main unit 201 and the reflecting part 213.

Next, the actual use of the apparatus and its action will be described below.

Figure 24:
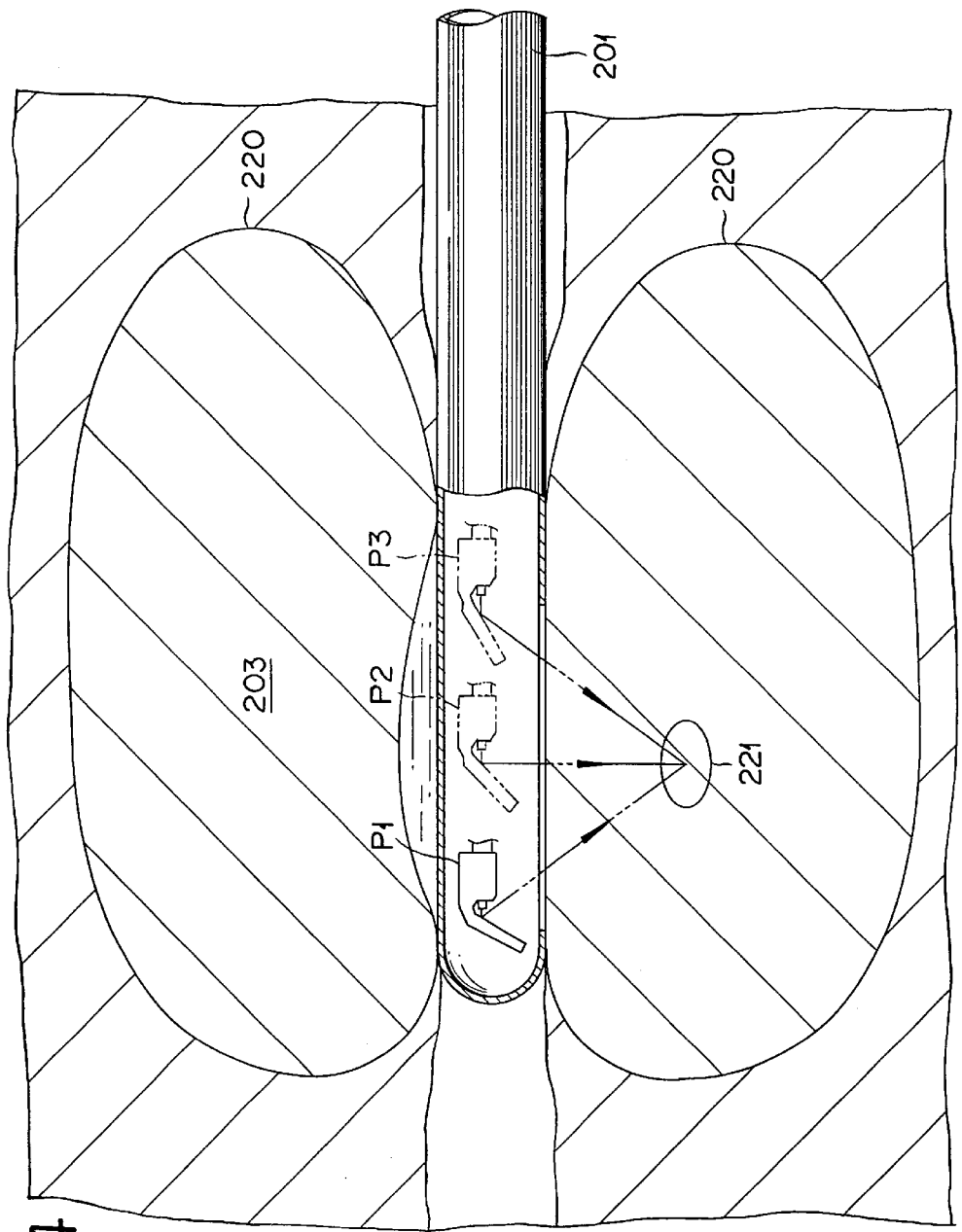
FIG. 24 is a schematic illustration of assistance in explaining the operating condition and action of the laser beam irradiation apparatus.

First, as shown in FIG. 24, the distal end of the main unit 201 is inserted into the urethra and the window 250 provided at its distal end is positioned in the vicinity of a target region 221 of a prostate 220, which is the lesional region. During the positioning, it is desirable to confirm the position of the window 250 directly using the endoscope 124. Next, while continuing the observation with the endoscope 124, the position of the emitting part relative to the target region 221 is adjusted by moving the entire apparatus in the longitudinal direction of the main unit 201, or turning the entire apparatus manually.

Next, the liquid is introduced into the balloon 203 via the lumen 261 by means of a feeding device in order to inflate the balloon 203. A cooling water circulating apparatus is started to circulate cooling water through the apparatus. Moore specifically, the cooling water flows into the distal end of the main unit 201 through a lumen 226 and cools various components inside the main unit 201 heated by the laser beam as well as the surface of the tissue contacting the cover 204.

The other side where the balloon 203 does not exist, i.e., the side where the window 250 is located, is fixed to the surface of the urethra by contacting to it due to the inflation of the balloon 203. Thus, the positional relation between the emitting part and the target region is fixed as the operator desired. Since the target region is determined to the intended direction and depth relative to the emitting part, the laser beam irradiation can be securely executed. In addition, the portion of the tissue that contacts with the cover 204 and the surface layer in its vicinity can be more securely protected from damages as the cooling water prevents their temperature increase.

Once the position is fixed, the operations of the laser beam generator and a motor 231 are started. The laser beam generated by the laser beam generator passes through the optical fiber 207 and enters the reflecting part 213. The reflecting part 213 reflects the laser beam sideway through the window 250 while reciprocating between the distal position P1 and the proximal position P3 via the middle position P2. During this operation, the optical axis of the laser beams cross at one point although the reflecting angle of the reflecting part 213 changes continuously. In other words, the laser beam is constantly aimed at the target region 221 inside the lesional region 220.

Thus, the target region 221 and its vicinity are heated by the laser beam and reach desired temperature. On the other hand, the irradiation time of the laser beam per unit area is short and the generated heat is small in the areas above the target region 221 such as the surface layer of the lesional region 220 and the areas below the target region 221. There fore the surrounding areas of the target region 221 are affected little by the laser beam so that the temperature is maintained relatively low. Consequently, the damages in the areas other than the target region 221 are either prevented or reduced, so that the patient's burden is alleviated. It is particularly advantageous as the damages of the surface layer can be prevented, in particular, when the target region 221 exists deep inside the tissues.

Next, laser beams will irradiate a different target region 221. By repeating this process, the entire area that constitutes the lesional region 220 can be treated.

According to the fourth embodiment, there is no need to have a special optical system to stabilize the spot diameter of the laser beam and the emitting part can be simplified. Therefore, it becomes easier to constantly maintain the function and performance of the apparatus to reduce the burden of the patient.

In addition to the above, the damage of the tissue of the surface that is in contact with the apparatus can be prevented to reduce the patient's burden. Although it is a simple structure, the damage of the normal tissue can be securely protected while effectively irradiating the lesional region located deep inside with the laser beam.

It is obvious that this invention is not limited to the particular embodiments shown and described above but may be variously changed and modified without departing from the technical concept of this invention.

As the material for the flat surface for reflecting the laser beam, a film made by laminating metal such as gold by means of vapor deposition or plating, or a multiple layer film consisting of dielectric materials can be preferably used. Said multiple layer film may be formed by vapor depositing a dielectric substance of high refractivity and a dielectric substance of low refractivity reciprocally multiple times. Dielectric substances of high refractivity include $Al_2O_3$, $ZrO_2$, $TiO_2$ and $CeO_2$, and dielectric substances of low refractivity include $MgF_2$ and $SiO_2$.

The laser beams to be used can be anything as long as they have depth-reaching capability against living organisms. However, the wavelengths of the laser beams are preferably 750 nm through 1300 nm or 1600 nm through 1800 nm. This is due to the fact that the laser beams in those wavelength ranges have particularly good depth-reaching capabilities and are not absorbed easily on the surface layer of living organisms. Consequently, the laser beams in said wavelength ranges can be more effectively applied to the target region of the lesional region located in deep areas of the tissue.

For example, gaseous lasers such as He-Ne laser, solid lasers such as Nd-YAG, and semiconductor lasers such as GaAlAs are applicable for the generators for generating laser beams in said wavelength ranges.

The material for the main unit is preferably a hard pipe made of metals such as stainless steel. The material for the wall members can be polyolefin such as polyethylene and polypropylene, ethylene-vinylacetate copolymer (EVA), polyvinyl chloride, polyester such as polyethylene terephthalate and polybutylene terephthalate, polyamide, polyurethane, polystyrene, polycarbonate, fluorocarbon resin, etc., or polymer alloy containing one of these, or a combination of them.

The cover and the light transmitting plate can be made of a material with a good light transmitting characteristic such as PET (polyethylene terephthalate), quartz glass, acryl, polystyrene, polycarbonate, polyethylene, polypropylene, vinylidene chloride, fluorocarbon resin, and polyester.

The main unit, balloon, and cover can be coated with lubrication materials such as hydrophilic polymer materials, silicon, and fluorocarbon resin. Such a lubricant reduces the surface friction of the part that is inserted into a body cavity so that it can be more smoothly inserted. It is also possible to use a disposable sheath to cover the main unit, and lubricate the surface of the sheath with such a lubricating material. This makes it possible to prevent the deterioration of lubricity due to peeling of lubrication coating resulting from multiple usages.

As the hydrophilic polymers, carboxymethyl cellulose, polysaccharides, polyvinyl alcohol, polyethylene oxide, sodium polyacrylate, methyl vinyl ether-maleic anhydride copolymer, or water soluble polyamide can be used preferably used, or, more preferably, methyl vinyl ether-maleic anhydride copolymer.

In case of using a laser beam irradiation apparatus having a main unit and a balloon covered with hydrophilic polymers, the main unit, the balloon and the cover are immersed, for example, into physiological saline. This makes the surface layers of the main unit and the balloon wetted and lubricated to reduce the frictions of the main unit and the balloon, and the patient's burden. For example, the insertion of the main unit into a body cavity, pulling out from the cavity, and the translation and rotation inside the body cavity can be done more smoothly.

As the energy to be irradiated against the tissue, other energies such as microwaves, radio frequency, and ultrasonic waves can be used as well in addition to laser beams.

Although prostate has been used as an example of the tissue to be treated in the above, but the tissues that can be treated with this apparatus include all tissues that can be irradiated with energies from within the body such as abdominal cavity or from the body surface, e.g. blood vessels, digestive tubes (esophagus, bowel, etc.).

This application is based on Japanese Patent Application No. 2000-201638 filed on Jul. 3, 2000, the contents of which are hereby incorporated by reference.

What is claimed is:

1. An energy irradiation apparatus for medical treatment of tissues through irradiation of energy comprising:
   a long main unit;
   an emitting part disposed moveably inside a distal end of said main unit for emitting energy transmitted to a distal side from a proximal side;
   a power transmission member disposed moveable inside said main unit, to a distal end of which is mounted said emitting part and having a proximal end at which a first engaging member is provided;
   a drive unit having a second engaging member which removably engages the first engaging member and a drive mechanism for reciprocating said second engaging member; and
   said main unit being removably engageable with said drive unit to form one body and permit the first and second engaging members to engage one another so that operation of the drive mechanism reciprocates the power transmission member.

2. An energy irradiation apparatus as claimed in claim 1, further comprising a restricting mechanism,
   in which either one of the first engaging member or the second engaging member has a hook with a substantially U-shaped groove,
   the other one of the first engaging member or the second engaging member comprises an indented narrow part, to which the groove fits, and guide parts formed in a tapered shape provided adjacent to the narrow part for leading the groove to the narrow part, and
   said restricting mechanism restricts motion of the first engaging member when leading the groove into the narrow part.

3. An energy irradiation apparatus as claimed in claim 1, in which said power transmission member also serves as a transmission member for transmitting the energy from the proximal side to the distal side.

4. An energy irradiation apparatus as claimed in claim 3, further comprising a casing with a supporting part by which the first engaging member is supported in such a way as to make a reciprocating motion, in which said power transmission member is stored in the casing making a loop.

5. An energy irradiation apparatus as claimed in claim 1, in which said energy is laser beam.

6. An energy irradiation apparatus as claimed in claim 1, in which said emitting part comprises a reflecting part for reflecting the energy transmitted to the distal side from the proximal side, said apparatus further comprising a guide mechanism having slide parts provided within a range required for the reciprocating motion of the reflecting part, and extension parts for tilting the reflecting part further toward a direction parallel to an axis of said main unit than it was engaged with the slide parts, and engaging with a portion of the reflecting part slidably to change an angle of the reflecting part as the reflecting part moves in the longitudinal direction, and an operating part provided on the proximal side for moving the reflecting part between a position where it engages with the slide parts and a position where it engages with the extension parts.

7. An energy irradiation apparatus as claimed in claim 6, in which said guide mechanism comprises connection parts in a substantially U-shape for connecting the slide parts with the extension parts.

8. An energy irradiation apparatus as claimed in claim 6, further comprising a lumen formed inside said main unit, in which an endoscope is disposed for observing vital tissues, and a linking mechanism having a supporting part for supporting the endoscope disposed in the lumen, in which said linking mechanism retracts the endoscope toward the proximal side when a portion of the reflecting part moves from the extension parts to the slide parts, and moves the endoscope toward the distal side when the same moves from the slide parts to the extension parts.

9. An energy irradiation apparatus as claimed in claim 6, further comprising a restricting mechanism for selectively allowing either the engagement between said reflecting part and the slide parts or the movement of the endoscope toward the distal side.

10. An energy irradiation apparatus as claimed in claim 6, in which said reflecting part is slidably connected to the vicinity of a distal end of a transmission member for transmitting the energy from the proximal side to the distal side, and said drive mechanism reciprocates the reflecting part in the longitudinal direction through said transmission member.

11. An energy irradiation apparatus as claimed in claim 6, in which the distal end of said main unit has an internal space for allowing the reflecting part to make a reciprocating motion, said guide mechanism consists of guide grooves formed on a pair of facing wall members in the internal space, and portions of the reflecting part have protrusions that are inserted into the guide grooves.

12. An energy irradiation apparatus as claimed in claim 6, in which said energy is laser beam.

13. An energy irradiation apparatus as claimed in claim 1, in which said emitting part comprises a fixed part fixed on said power transmission member, a reflecting part having a flat surface for reflecting the energy emitted from the distal end of said power transmission member, and a flexing part placed between the fixed part and the reflecting part, and makes a reciprocating motion accompanied by said power transmission member, said apparatus further comprising an angle changing mechanism for changing a reflecting angle of the flat surface by repetitively flexing the flexing part repeated in accordance with the reciprocating motion of the emitting part.

14. An energy irradiation apparatus as claimed in claim 13, in which said flexing part has a groove on a first surface located on the flat surface side and flexes repetitively around the groove.

15. An energy irradiation apparatus as claimed in claim 14, in which said groove has an edge formed on its bottom.

16. An energy irradiation apparatus as claimed in claim 15, in which said flexing part has a groove with an edge formed on a bottom of a second surface facing opposite to the first surface, and a distance between the tip of the edge of the first surface and the fixed part is longer than a distance between a tip of the edge of the second surface.

17. An energy irradiation apparatus as claimed in claim 13, in which said emitting part is integrally formed.

18. An energy irradiation apparatus as claimed in claim 13, in which said angle changing mechanism consists of guide grooves that are not parallel to an axial direction of said main unit and formed on a housing of said main unit, and protrusions formed on side surfaces of the reflecting part to engage with the guide grooves.

19. An energy irradiation apparatus as claimed in claim 13, in which the sum of an incident angle and the reflecting angle is less than 90 degrees when the reflecting part is located at a distal position, and greater than 90 degrees when it is located at a proximal position.

20. An energy irradiation apparatus as claimed in claim 13, in which axes of the energy reflected by the flat surface always cross at one point each other regardless of positioning of the reflecting part.

21. An energy irradiation apparatus as claimed in claim 13, in which said energy is laser beam and said power transmission member comprises an energy transmission member having a proximal end, into which the energy is introduced, and a distal end, from which the energy is emitted.

22. An energy irradiation apparatus for medical treatment of tissues through irradiation of energy comprising:

an elongated main unit;

an emitting part movably disposed in a distal end portion of said main unit to emit energy;

a power transmission member movably disposed inside said main unit and having a distal end portion at which is located said emitting part;

a drive mechanism operable to longitudinally move the power transmission member relative to the main unit;

a first engaging member provided at said power transmission member for receiving a drive force from said drive mechanism; and a second engaging member provided at said drive mechanism and removably engageable with the first engaging member so that engagement of said first and second engaging members with one another causes the power transmission member to receive the driving force from the drive mechanism to longitudinally move the power transmission member.

* * * * *